United States Patent
Nathwani et al.

(10) Patent No.: US 11,306,142 B2
(45) Date of Patent: Apr. 19, 2022

(54) BISPECIFIC ANTIBODIES TO ROR1 AND CD3

(71) Applicant: UCL Business LTD, London (GB)

(72) Inventors: Amit Nathwani, London (GB); Satyen Gohil, London (GB); Marco Della Peruta, London (GB)

(73) Assignee: UCL Business LTD, London (GB)

( * ) Notice: Subject to any disclaimer, the term of this patent is extended or adjusted under 35 U.S.C. 154(b) by 0 days.

(21) Appl. No.: 16/628,404

(22) PCT Filed: Jul. 5, 2018

(86) PCT No.: PCT/GB2018/051916
§ 371 (c)(1),
(2) Date: Jan. 3, 2020

(87) PCT Pub. No.: WO2019/008379
PCT Pub. Date: Jan. 10, 2019

(65) Prior Publication Data
US 2020/0157218 A1     May 21, 2020

(30) Foreign Application Priority Data
Jul. 5, 2017   (GB) ..................... 1710838

(51) Int. Cl.
*C07K 16/28*   (2006.01)
*A61P 35/00*   (2006.01)

(52) U.S. Cl.
CPC .......... *C07K 16/2809* (2013.01); *A61P 35/00* (2018.01); *C07K 2317/24* (2013.01); *C07K 2317/31* (2013.01); *C07K 2317/33* (2013.01); *C07K 2317/34* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 8,076,459 B2 | 12/2011 | Hofmeister et al. | |
| 9,102,736 B2 | 8/2015 | Hofmeister et al. | |
| 2013/0273073 A1 | 10/2013 | Kipps et al. | |
| 2013/0281922 A1 | 10/2013 | Teige | |
| 2015/0306141 A1 | 10/2015 | Jensen et al. | |
| 2016/0017058 A1* | 1/2016 | Kim ..................... | A61K 47/542 424/136.1 |
| 2016/0297881 A1* | 10/2016 | Vu ..................... | C07K 16/3015 |
| 2020/0030454 A1 | 1/2020 | Lannutti et al. | |

FOREIGN PATENT DOCUMENTS

| | | |
|---|---|---|
| EP | 2789630 A1 | 10/2014 |
| WO | WO-2005/040220 A1 | 5/2005 |
| WO | WO-2007/146957 A2 | 12/2007 |
| WO | WO-2010/124188 A1 | 10/2010 |
| WO | WO-2011/054007 A1 | 5/2011 |
| WO | WO-2011/079902 A2 | 7/2011 |
| WO | WO-2012/045085 A1 | 4/2012 |
| WO | WO-2012/075158 A1 | 6/2012 |
| WO | WO-2012/076066 A1 | 6/2012 |
| WO | WO-2012/076727 A1 | 6/2012 |
| WO | WO-2014/031174 A1 | 2/2014 |
| WO | WO-2014/167022 A1 | 10/2014 |
| WO | WO-2015/184203 A1 | 12/2015 |
| WO | WO-2015/184207 A1 | 12/2015 |
| WO | WO-2016/016343 A1 | 2/2016 |
| WO | WO-2016/016344 A1 | 2/2016 |
| WO | WO-2016/039321 A1 | 3/2016 |
| WO | WO-2016/055592 A1 | 4/2016 |
| WO | WO-2016/055593 A1 | 4/2016 |
| WO | WO-2016/094873 A2 | 6/2016 |
| WO | WO-2016/115559 A1 | 7/2016 |
| WO | WO-2016/124553 A1 | 8/2016 |
| WO | WO-2016/187216 A1 | 11/2016 |
| WO | WO-2016/187220 A2 | 11/2016 |
| WO | WO-2017/072361 A1 | 5/2017 |
| WO | WO-2017/127499 A1 | 7/2017 |
| WO | WO-2017/127664 A1 | 7/2017 |
| WO | WO-2017/142928 A1 | 8/2017 |
| WO | WO-2017/156479 A1 | 9/2017 |
| WO | WO-2018/011138 A1 | 1/2018 |
| WO | WO-2018/119314 A1 | 6/2018 |
| WO | WO-2018/217799 A1 | 11/2018 |
| WO | WO-2018/237335 A1 | 12/2018 |
| WO | WO-2019/005636 A2 | 1/2019 |
| WO | WO-2019/005638 A2 | 1/2019 |
| WO | WO-2019/016381 A1 | 1/2019 |

(Continued)

OTHER PUBLICATIONS

Barat, B. et al., Development of a Humanized ROR1×CD3 Bispecific DART Molecule for the Treatment of Solid and Liquid Tumors, presented at the 2016 American Association for Cancer Research Annual Meeting, one page, Apr. 16-20, 2016.
Baskar, S. et al., Targeting malignant B cells with an immunotoxin against ROR1, mAbs, 4:3, 349-361 (2012).
Daneshmanesh, A. et al., Monoclonal antibodies against ROR1 induce apoptosis of chronic lymphocytic leukemia (CLL) cells, Leukemia, 26:1348-1355 (2012).
Deniger, D. et al., Sleeping Beauty Transposition of Chimeric Antigen Receptors largeting Receptor Tyrosine Kinase-Like Orphan Receptor-1 (ROR1) into Diverse Memory I-Cell Populations, PLOS One, 10(6): 19 pages (2015).
Gohil, S. et al., An ROR1 bi-specific T-cell engager provides effective targeting and cytotoxicity against a range of solid tumors, Oncoimmunology, 6(7):e1326437, 11 pages (2017).
Gohil, S. et al., Preclinical development of novel humanised ROR1 targeting chimeric antigen receptor T cells and bispecific T-cell engagers, Poster Abstracts, one page (2017).

(Continued)

*Primary Examiner* — Elly-Gerald Stoica
(74) *Attorney, Agent, or Firm* — Choate, Hall & Stewart LLP; Brenda Herschbach Jarrell; Melissa M. Adams

(57) ABSTRACT

There is described bispecific antibodies which selectively bind to Receptor Tyrosine Kinase Like Orphan Receptor 1 (ROR1) and the CD3 subunit of the T-Cell Receptor (TCR), their production and their use. Also described is the use of the bispecific antibodies in the treatment of cancer.

Figure 1:
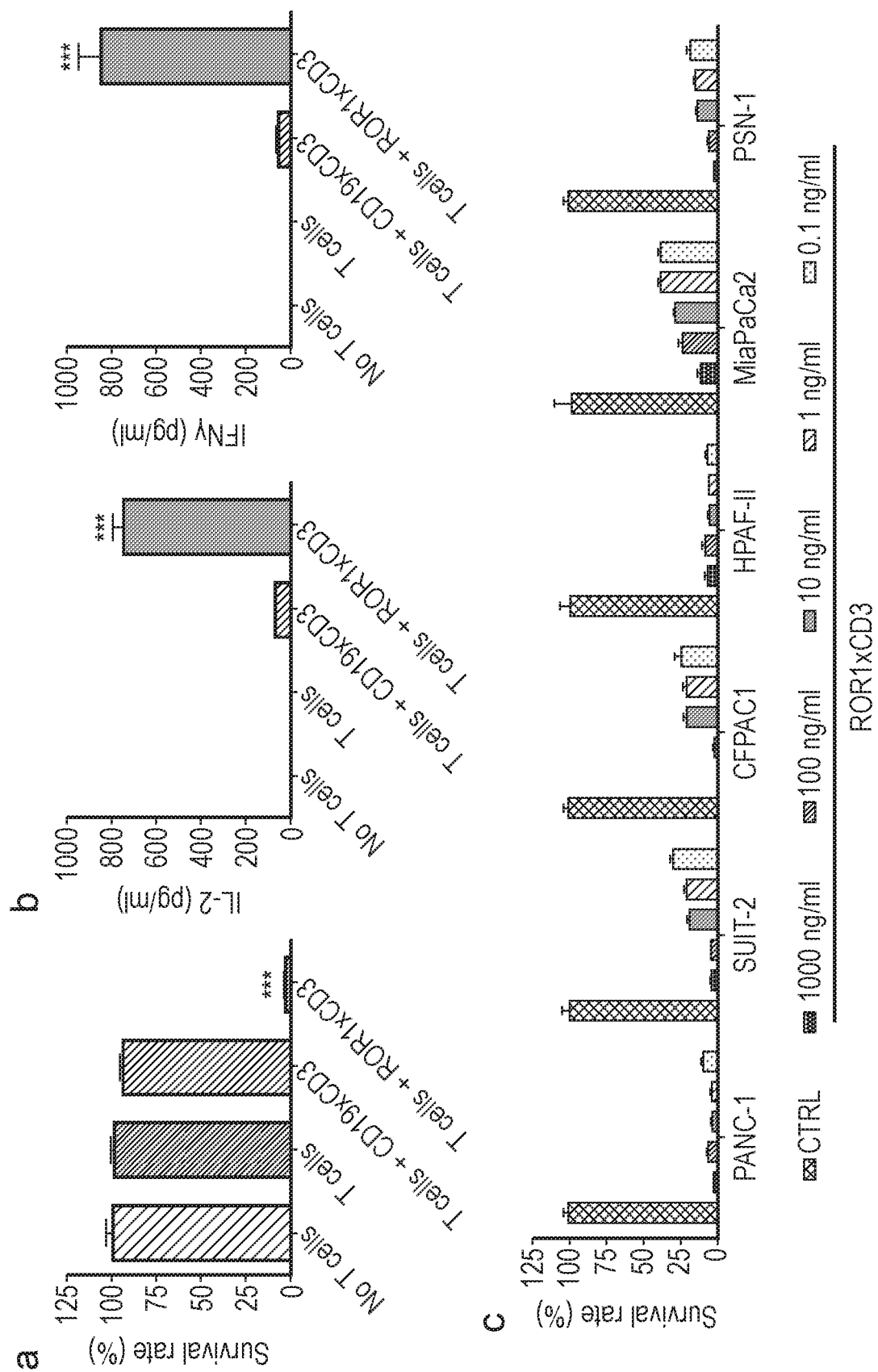

16 Claims, 3 Drawing Sheets
Specification includes a Sequence Listing.

(56) References Cited

FOREIGN PATENT DOCUMENTS

| WO | WO-2019/030223 A1 | 2/2019 |
|----|-------------------|--------|
| WO | WO-2019/030240 A1 | 2/2019 |
| WO | WO-2019/090110 A1 | 5/2019 |
| WO | WO-2019/122445 A1 | 6/2019 |
| WO | WO-2019/122447 A1 | 6/2019 |
| WO | WO-2019/225992 A1 | 11/2019 |

OTHER PUBLICATIONS

Hudecek, M. et al., Receptor Affinity and Extracellular Domain Modifications Affect Tumor Recognition by ROR1-Specific Chimeric Antigen Receptor T Cells, Clinical Cancer Research, 19(12):3153-3164 (2013).

Kershaw, M. et al., A Phase I Study on Adoptive Immunotherapy Using Gene-Modified T Cells for Ovarian Cancer, Clinical Cancer Research, 12:6106-6115 (2006).

Lamers, C. et al., Process validation and clinical evaluation of a protocol to generate gene-modified T lymphocytes for umunogene therapy for metastatic renal cell carcinoma: GMP-controlled transduction and expansion of patient's T lymphocytes using a carboxy anhydrase IX-specific scFv transgene, Cytotherapy, 8(6):542-553 (2006).

Maus, M. et al., T Cells Expressing Chimeric ANtigen Receptors Can Cause Anaphylaxis in Humans, Cancer Immunology Research, 1(1):26-31 (2013).

Paredes-Moscosso, S. et al., Novel ROR1 Antibody Is Able to Irigger Specific and Superior Complemente-Dependent Cytotoxicity (CDC) on Primary CLL Cells, Blood, 128(22):2052, 4 pages (2016).

Paredes-Moscosso, Solange Rosa, ROR1 as a Target for Cancer Immunotherapy, A thesis sumbitted to University College London (UCL) for the degree of Doctor of Philosophy, 305 pages (2017).

Gohil, S. et al., Pre-clinical development of novel ROR1 chimeric antigen receptor T cells and bispecific T cell engagers, 212 pages (Mar. 1, 2019).

Gohil et al., A Novel Humanised ROR1 Bi-Specific T-Cell Engager Molecule for the Treatment of Chronic Lymphocytic Leukaemia, Blood (Dec. 2, 2016), 128(22):3244, 642. CLL: Therapy, Excluding Transplantation: Poster II (<https://doi.org/10.1182/blood.V128.22.3244.3244>).

Gohil et al., A ROR1 Bispecific T Cell Engager for the Treatment of Chronic Lymphocytic Leukaemia Demonstrates Enhanced Function Following Ibrutinib Treatment, Blood (Dec. 7, 2017), 130(Supplement 1):4316, 642. CLL: Therapy, Excluding Transplantation: Poster III (<https://doi.org/10.1182/blood.V130.Suppl_1.4316.4316>).

Gohil et al., Novel Humanised ROR1 Chimeric Antigen Receptors for the Treatment of Haematological Malignancies, Blood (Dec. 2, 2016), 128(22):3361, 703. Adoptive Immunotherapy Poster II (<http://doi.org/10.1182/blood.V128.22.3361.3361>).

* cited by examiner

SEQUENCE LISTING

<160> NUMBER OF SEQ ID NOS: 76

<210> SEQ ID NO 1
<211> LENGTH: 5
<212> TYPE: PRT
<213> ORGANISM: Artificial sequence
<220> FEATURE:
<223> OTHER INFORMATION: Linker

<400> SEQUENCE: 1

Gly Gly Gly Gly Ser
1               5

<210> SEQ ID NO 2
<211> LENGTH: 10
<212> TYPE: PRT
<213> ORGANISM: Artificial sequence
<220> FEATURE:
<223> OTHER INFORMATION: Linker

<400> SEQUENCE: 2

Gly Gly Gly Gly Ser Gly Gly Gly Gly Ser
1               5                   10

<210> SEQ ID NO 3
<211> LENGTH: 107
<212> TYPE: PRT
<213> ORGANISM: Rattus norvegicus

<400> SEQUENCE: 3

Asp Ile Gln Met Thr Gln Ser Pro Ser Phe Leu Ser Ala Ser Val Gly
1               5                   10                  15

```
Asp Arg Val Thr Ile Asn Cys Lys Ala Ser Gln Asn Ile Asp Arg Tyr
            20                  25                  30

Leu Asn Trp Tyr Gln Gln Lys Leu Gly Glu Ala Pro Lys Arg Leu Leu
        35                  40                  45

Tyr Asn Thr Asn Lys Leu Gln Thr Gly Ile Pro Ser Arg Phe Ser Gly
    50                  55                  60

Ser Gly Ser Ala Thr Asp Phe Thr Leu Thr Ile Ser Ser Leu Gln Pro
65                  70                  75                  80

Glu Asp Phe Ala Thr Tyr Phe Cys Leu Gln Tyr Asn Ser Leu Pro Leu
                85                  90                  95

Thr Phe Gly Ser Gly Thr Lys Leu Glu Ile Lys
            100                 105

<210> SEQ ID NO 4
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Arg Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105

<210> SEQ ID NO 5
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Phe Gln Gln Lys Pro Gly Lys Ala Pro Lys Ser Leu Ile
        35                  40                  45

Tyr Asn Thr Asn Lys Leu Gln Thr Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Arg Leu Glu Ile Lys
            100                 105
```

```
<210> SEQ ID NO 6
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Leu Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 7

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Ile Asp Arg Tyr
            20                  25                  30

Leu Asn Trp Tyr Gln Gln Lys Pro Gly Lys Ala Pro Lys Leu Leu Ile
        35                  40                  45

Tyr Asn Thr Asn Lys Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Leu Pro Leu
                85                  90                  95

Thr Phe Gly Gln Gly Thr Lys Leu Glu Ile Lys
            100                 105

<210> SEQ ID NO 8
<211> LENGTH: 107
<212> TYPE: PRT
<213> ORGANISM: Artificial sequence
<220> FEATURE:
<223> OTHER INFORMATION: Humanised light chain variable region

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Lys Ala Ser Gln Asn Ile Asp Arg Tyr
            20                  25                  30
```

Leu Asn Trp Tyr Gln Gln Lys Pro Gly Lys Ala Pro Lys Leu Leu Ile
              35                  40                  45

Tyr Asn Thr Asn Lys Leu Gln Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Leu Gln Tyr Asn Ser Leu Pro Leu
                 85                  90                  95

Thr Phe Gly Gln Gly Thr Lys Leu Glu Ile Lys
                100                 105

<210> SEQ ID NO 9
<211> LENGTH: 117
<212> TYPE: PRT
<213> ORGANISM: Rattus norvegicus

<400> SEQUENCE: 9

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Ile Phe Ser Glu His
                 20                  25                  30

Asn Met Ala Trp Val Arg Gln Ala Pro Lys Lys Gly Leu Glu Trp Val
             35                  40                  45

Ala Thr Ile Ser Asp Asp Gly Arg Asn Thr Tyr Tyr Arg Asp Ser Met
 50                  55                  60

Arg Gly Arg Phe Thr Ile Ser Arg Glu Asn Ala Arg Ser Thr Leu Tyr
 65                  70                  75                  80

Leu Gln Leu Asp Ser Leu Arg Ser Glu Asp Thr Ala Tyr Tyr Cys
                 85                  90                  95

Ala Ser His Arg Tyr Asn Leu Phe Asp Ser Trp Gly Gln Gly Val Met
                100                 105                 110

Val Thr Val Ser Ser
                115

<210> SEQ ID NO 10
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 10

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ile Phe Ser Glu His
                 20                  25                  30

Asn Met Ala Trp Val Arg Gln Ala Pro Gly Lys Gly Leu Glu Trp Val
             35                  40                  45

Ala Thr Ile Ser Asp Asp Gly Arg Asn Thr Tyr Tyr Arg Asp Ser Met
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Ser His Arg Tyr Asn Leu Phe Asp Ser Trp Gly Gln Gly Thr Met
                100                 105                 110

Val Thr Val Ser Ser
        115

<210> SEQ ID NO 11
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
        35                  40                  45

Ser Thr Ile Ser Asp Asp Gly Arg Asn Thr Tyr Tyr Arg Asp Ser Met
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Arg Tyr Asn Leu Phe Asp Ser Trp Gly Gln Gly Thr Leu
            100                 105                 110

Val Thr Val Ser Ser
        115

<210> SEQ ID NO 12
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
        35                  40                  45

Ala Thr Ile Ser Asp Asp Gly Arg Asn Thr Tyr Tyr Arg Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Arg Tyr Asn Leu Phe Asp Ser Trp Gly Gln Gly Thr Met
            100                 105                 110

Val Thr Val Ser Ser
        115

<210> SEQ ID NO 13
<211> LENGTH: 117
<212> TYPE: PRT
<213> ORGANISM: Artificial sequence
<220> FEATURE:
<223> OTHER INFORMATION: Humanised heavy chain variable region

```
<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Val Trp Val
        35                  40                  45

Ser Thr Ile Ser Asp Asp Gly Arg Asn Thr Tyr Tyr Arg Asp Ser Met
    50                  55                  60

Arg Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Tyr Asn Leu Phe Asp Ser Trp Gln Gly Thr Leu
            100                 105                 110

Val Thr Val Ser Ser
            115

<210> SEQ ID NO 14
<211> LENGTH: 117
<212> TYPE: PRT
<213> ORGANISM: Artificial sequence
<220> FEATURE:
<223> OTHER INFORMATION: Humanised heavy chain variable region

<400> SEQUENCE: 14

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
        35                  40                  45

Ser Thr Ile Ser Asp Asp Gly Arg Asn Thr Tyr Tyr Arg Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys His Arg Tyr Asn Leu Phe Asp Ser Trp Gln Gly Thr Leu
            100                 105                 110

Val Thr Val Ser Ser
            115

<210> SEQ ID NO 15
<211> LENGTH: 26
<212> TYPE: PRT
<213> ORGANISM: Rattus norvegicus

<400> SEQUENCE: 15

Asp Ile Gln Met Thr Gln Ser Pro Ser Phe Leu Ser Ala Ser Val Gly
1               5                   10                  15

Asp Arg Val Thr Ile Asn Cys Lys Ala Ser
            20                  25

<210> SEQ ID NO 16
<211> LENGTH: 6
<212> TYPE: PRT
```

-continued

<213> ORGANISM: Rattus norvegicus

<400> SEQUENCE: 16

```
Gln Asn Ile Asp Arg Tyr
1               5
```

<210> SEQ ID NO 17
<211> LENGTH: 17
<212> TYPE: PRT
<213> ORGANISM: Rattus norvegicus

<400> SEQUENCE: 17

```
Leu Asn Trp Tyr Gln Gln Lys Leu Gly Glu Ala Pro Lys Arg Leu Leu
1               5                   10                  15

Tyr
```

<210> SEQ ID NO 18
<211> LENGTH: 3
<212> TYPE: PRT
<213> ORGANISM: Rattus norvegicus

<400> SEQUENCE: 18

```
Asn Thr Asn
1
```

<210> SEQ ID NO 19
<211> LENGTH: 36
<212> TYPE: PRT
<213> ORGANISM: Rattus norvegicus

<400> SEQUENCE: 19

```
Lys Leu Gln Thr Gly Ile Pro Ser Arg Phe Ser Gly Ser Gly Ser Ala
1               5                   10                  15

Thr Asp Phe Thr Leu Thr Ile Ser Ser Leu Gln Pro Glu Asp Phe Ala
            20                  25                  30

Thr Tyr Phe Cys
        35
```

<210> SEQ ID NO 20
<211> LENGTH: 9
<212> TYPE: PRT
<213> ORGANISM: Rattus norvegicus

<400> SEQUENCE: 20

```
Leu Gln Tyr Asn Ser Leu Pro Leu Thr
1               5
```

<210> SEQ ID NO 21
<211> LENGTH: 10
<212> TYPE: PRT
<213> ORGANISM: Rattus norvegicus

<400> SEQUENCE: 21

```
Phe Gly Ser Gly Thr Lys Leu Glu Ile Lys
1               5                   10
```

<210> SEQ ID NO 22
<211> LENGTH: 25
<212> TYPE: PRT
<213> ORGANISM: Rattus norvegicus

<400> SEQUENCE: 22

Glu Val Gln Leu Val Glu Ser Gly Gly Gly Leu Val Gln Pro Gly Arg
1               5                   10                  15

Ser Leu Lys Leu Ser Cys Ala Ala Ser
            20                  25

<210> SEQ ID NO 23
<211> LENGTH: 8
<212> TYPE: PRT
<213> ORGANISM: Rattus norvegicus

<400> SEQUENCE: 23

Gly Phe Ile Phe Ser Glu His Asn
1               5

<210> SEQ ID NO 24
<211> LENGTH: 17
<212> TYPE: PRT
<213> ORGANISM: Rattus norvegicus

<400> SEQUENCE: 24

Met Ala Trp Val Arg Gln Ala Pro Lys Lys Gly Leu Glu Trp Val Ala
1               5                   10                  15

Thr

<210> SEQ ID NO 25
<211> LENGTH: 8
<212> TYPE: PRT
<213> ORGANISM: Rattus norvegicus

<400> SEQUENCE: 25

Ile Ser Asp Asp Gly Arg Asn Thr
1               5

<210> SEQ ID NO 26
<211> LENGTH: 38
<212> TYPE: PRT
<213> ORGANISM: Rattus norvegicus

<400> SEQUENCE: 26

Tyr Tyr Arg Asp Ser Met Arg Gly Arg Phe Thr Ile Ser Arg Glu Asn
1               5                   10                  15

Ala Arg Ser Thr Leu Tyr Leu Gln Leu Asp Ser Leu Arg Ser Glu Asp
            20                  25                  30

Thr Ala Thr Tyr Tyr Cys
        35

<210> SEQ ID NO 27
<211> LENGTH: 10
<212> TYPE: PRT
<213> ORGANISM: Rattus norvegicus

<400> SEQUENCE: 27

Ala Ser His Arg Tyr Asn Leu Phe Asp Ser
1               5                   10

<210> SEQ ID NO 28
<211> LENGTH: 11
<212> TYPE: PRT
<213> ORGANISM: Rattus norvegicus

```
<400> SEQUENCE: 28

Trp Gly Gln Gly Val Met Val Thr Val Ser Ser
1               5                   10

<210> SEQ ID NO 29
<211> LENGTH: 26
<212> TYPE: PRT
<213> ORGANISM: Homo sapiens

<400> SEQUENCE: 29

Asp Ile Gln Met Thr Gln Ser Pro Ser Leu Ser Ala Ser Val Gly
1               5                   10                  15

Asp Arg Val Thr Ile Thr Cys Lys Ala Ser
            20                  25

<210> SEQ ID NO 30
<211> LENGTH: 17
<212> TYPE: PRT
<213> ORGANISM: Homo sapiens

<400> SEQUENCE: 30

Leu Asn Trp Tyr Gln Gln Lys Pro Gly Lys Ala Pro Lys Arg Leu Ile
1               5                   10                  15

Tyr

<210> SEQ ID NO 31
<211> LENGTH: 36
<212> TYPE: PRT
<213> ORGANISM: Homo sapiens

<400> SEQUENCE: 31

Lys Leu Gln Thr Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 32
<211> LENGTH: 10
<212> TYPE: PRT
<213> ORGANISM: Homo sapiens

<400> SEQUENCE: 32

Phe Gly Gln Gly Thr Lys Leu Glu Ile Lys
1               5                   10

<210> SEQ ID NO 33
<211> LENGTH: 25
<212> TYPE: PRT
<213> ORGANISM: Homo sapiens

<400> SEQUENCE: 33

Gln Val Gln Leu Val Glu Ser Gly Gly Val Val Gln Pro Gly Arg
1               5                   10                  15

Ser Leu Arg Leu Ser Cys Ala Ala Ser
            20                  25

<210> SEQ ID NO 34
<211> LENGTH: 17
<212> TYPE: PRT
```

```
<213> ORGANISM: Homo sapiens

<400> SEQUENCE: 34

Met Ala Trp Val Arg Gln Ala Pro Gly Lys Gly Leu Glu Trp Val Ala
1               5                   10                  15
Thr

<210> SEQ ID NO 35
<211> LENGTH: 40
<212> TYPE: PRT
<213> ORGANISM: Homo sapiens

<400> SEQUENCE: 35

Tyr Tyr Arg Asp Ser Met Arg Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Thr Ser
        35                  40

<210> SEQ ID NO 36
<211> LENGTH: 10
<212> TYPE: PRT
<213> ORGANISM: Artificial sequence
<220> FEATURE:
<223> OTHER INFORMATION: Humanised heavy chain CDR3

<400> SEQUENCE: 36

Thr Ser His Arg Tyr Asn Leu Phe Asp Ser
1               5                   10

<210> SEQ ID NO 37
<211> LENGTH: 11
<212> TYPE: PRT
<213> ORGANISM: Homo sapiens

<400> SEQUENCE: 37

Trp Gly Gln Gly Thr Met Val Thr Val Ser Ser
1               5                   10

<210> SEQ ID NO 38
<211> LENGTH: 17
<212> TYPE: PRT
<213> ORGANISM: Homo sapiens

<400> SEQUENCE: 38

Leu Asn Trp Phe Gln Gln Lys Pro Gly Lys Ala Pro Lys Ser Leu Ile
1               5                   10                  15
Tyr

<210> SEQ ID NO 39
<211> LENGTH: 36
<212> TYPE: PRT
<213> ORGANISM: Homo sapiens

<400> SEQUENCE: 39

Lys Leu Gln Thr Gly Val Pro Ser Lys Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35
```

<210> SEQ ID NO 40
<211> LENGTH: 10
<212> TYPE: PRT
<213> ORGANISM: Homo sapiens

<400> SEQUENCE: 40

Phe Gly Gln Gly Thr Arg Leu Glu Ile Lys
1               5                   10

<210> SEQ ID NO 41
<211> LENGTH: 25
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 42
<211> LENGTH: 17
<212> TYPE: PRT
<213> ORGANISM: Homo sapiens

<400> SEQUENCE: 42

Met Ala Trp Val Arg Gln Ala Pro Gly Lys Gly Leu Glu Trp Val Ser
1               5                   10                  15

Thr

<210> SEQ ID NO 43
<211> LENGTH: 40
<212> TYPE: PRT
<213> ORGANISM: Homo sapiens

<400> SEQUENCE: 43

Tyr Tyr Arg Asp Ser Met Arg Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys Ala Lys
        35                  40

<210> SEQ ID NO 44
<211> LENGTH: 10
<212> TYPE: PRT
<213> ORGANISM: Artificial sequence
<220> FEATURE:
<223> OTHER INFORMATION: Humanised heavy chain CDR3

<400> SEQUENCE: 44

Ala Lys His Arg Tyr Asn Leu Phe Asp Ser
1               5                   10

<210> SEQ ID NO 45
<211> LENGTH: 11
<212> TYPE: PRT
<213> ORGANISM: Homo sapiens

<400> SEQUENCE: 45

Trp Gly Gln Gly Thr Leu Val Thr Val Ser Ser
1               5                   10

<210> SEQ ID NO 46
<211> LENGTH: 17
<212> TYPE: PRT
<213> ORGANISM: Homo sapiens

<400> SEQUENCE: 46

Leu Asn Trp Tyr Gln Gln Lys Pro Gly Lys Ala Pro Lys Leu Leu Ile
1               5                   10                  15

Tyr

<210> SEQ ID NO 47
<211> LENGTH: 36
<212> TYPE: PRT
<213> ORGANISM: Homo sapiens

<400> SEQUENCE: 47

Lys Leu Gln Thr Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
            35

<210> SEQ ID NO 48
<211> LENGTH: 40
<212> TYPE: PRT
<213> ORGANISM: Homo sapiens

<400> SEQUENCE: 48

Tyr Tyr Arg Asp Ser Met Arg Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys Ala Arg
            35                  40

<210> SEQ ID NO 49
<211> LENGTH: 10
<212> TYPE: PRT
<213> ORGANISM: Artificial sequence
<220> FEATURE:
<223> OTHER INFORMATION: Humanised heavy chain CDR3

<400> SEQUENCE: 49

Ala Arg His Arg Tyr Asn Leu Phe Asp Ser
1               5                   10

<210> SEQ ID NO 50
<211> LENGTH: 26
<212> TYPE: PRT
<213> ORGANISM: Homo sapiens

<400> SEQUENCE: 50

Asp Ile Gln Leu Thr Gln Ser Pro Ser Phe Leu Ser Ala Ser Val Gly
1               5                   10                  15

Asp Arg Val Thr Ile Thr Cys Lys Ala Ser
            20                  25

<210> SEQ ID NO 51
<211> LENGTH: 17
<212> TYPE: PRT

```
<213> ORGANISM: Homo sapiens

<400> SEQUENCE: 51

Met Ala Trp Val Arg Gln Ala Pro Gly Lys Gly Leu Val Trp Val Ser
1               5                   10                  15

Thr

<210> SEQ ID NO 52
<211> LENGTH: 40
<212> TYPE: PRT
<213> ORGANISM: Homo sapiens

<400> SEQUENCE: 52

Tyr Tyr Arg Asp Ser Met Arg Gly Arg Phe Thr Ile Ser Arg Asp Asn
1               5                   10                  15

Ala Lys Asn Thr Leu Tyr Leu Gln Met Asn Ser Leu Arg Ala Glu Asp
            20                  25                  30

Thr Ala Val Tyr Tyr Cys Ala Arg
        35                  40

<210> SEQ ID NO 53
<211> LENGTH: 26
<212> TYPE: PRT
<213> ORGANISM: Homo sapiens

<400> SEQUENCE: 53

Asp Ile Gln Met Thr Gln Ser Pro Ser Thr Leu Ser Ala Ser Val Gly
1               5                   10                  15

Asp Arg Val Thr Ile Thr Cys Lys Ala Ser
            20                  25

<210> SEQ ID NO 54
<211> LENGTH: 36
<212> TYPE: PRT
<213> ORGANISM: Homo sapiens

<400> SEQUENCE: 54

Lys Leu Gln Thr Gly Val Pro Ser Arg Phe Ser Gly Ser Gly Ser Gly
1               5                   10                  15

Thr Glu Phe Thr Leu Thr Ile Ser Ser Leu Gln Pro Asp Asp Phe Ala
            20                  25                  30

Thr Tyr Tyr Cys
        35

<210> SEQ ID NO 55
<211> LENGTH: 25
<212> TYPE: PRT
<213> ORGANISM: Homo sapiens

<400> SEQUENCE: 55

Glu Val Gln Leu Val Glu Ser Gly Gly Gly Leu Val Gln Pro Gly Arg
1               5                   10                  15

Ser Leu Arg Leu Ser Cys Ala Ala Ser
            20                  25

<210> SEQ ID NO 56
<211> LENGTH: 40
<212> TYPE: PRT
<213> ORGANISM: Homo sapiens
```

<400> SEQUENCE: 56

Tyr Tyr Arg Asp Ser Met Arg Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Leu Tyr Tyr Cys Ala Lys
        35                  40

<210> SEQ ID NO 57
<211> LENGTH: 10
<212> TYPE: PRT
<213> ORGANISM: Artificial sequence
<220> FEATURE:
<223> OTHER INFORMATION: Heavy chain CDR3
<220> FEATURE:
<221> NAME/KEY: misc_feature
<222> LOCATION: (1)..(1)
<223> OTHER INFORMATION: Xaa can be Ala or Thr
<220> FEATURE:
<221> NAME/KEY: misc_feature
<222> LOCATION: (2)..(2)
<223> OTHER INFORMATION: Xaa can be Ser, Lys or Arg

<400> SEQUENCE: 57

Xaa Xaa His Arg Tyr Asn Leu Phe Asp Ser
1               5                   10

<210> SEQ ID NO 58
<211> LENGTH: 11
<212> TYPE: PRT
<213> ORGANISM: Rattus norvegicus

<400> SEQUENCE: 58

Lys Ala Ser Gln Asn Ile Asp Arg Tyr Leu Asn
1               5                   10

<210> SEQ ID NO 59
<211> LENGTH: 7
<212> TYPE: PRT
<213> ORGANISM: Rattus norvegicus

<400> SEQUENCE: 59

Asn Thr Asn Lys Leu Gln Thr
1               5

<210> SEQ ID NO 60
<211> LENGTH: 5
<212> TYPE: PRT
<213> ORGANISM: Rattus norvegicus

<400> SEQUENCE: 60

Glu His Asn Met Ala
1               5

<210> SEQ ID NO 61
<211> LENGTH: 17
<212> TYPE: PRT
<213> ORGANISM: Rattus norvegicus

<400> SEQUENCE: 61

Thr Ile Ser Asp Asp Gly Arg Asn Thr Tyr Tyr Arg Asp Ser Met Arg
1               5                   10                  15

Gly

```
<210> SEQ ID NO 62
<211> LENGTH: 8
<212> TYPE: PRT
<213> ORGANISM: Rattus norvegicus

<400> SEQUENCE: 62

His Arg Tyr Asn Leu Phe Asp Ser
1               5

<210> SEQ ID NO 63
<211> LENGTH: 106
<212> TYPE: PRT
<213> ORGANISM: Mus musculus

<400> SEQUENCE: 63

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105

<210> SEQ ID NO 64
<211> LENGTH: 106
<212> TYPE: PRT
<213> ORGANISM: Artificial sequence
<220> FEATURE:
<223> OTHER INFORMATION: Humanised light chain variable region

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

Asn Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 65
<211> LENGTH: 106
<212> TYPE: PRT
<213> ORGANISM: Artificial sequence
<220> FEATURE:
<223> OTHER INFORMATION: Humanised light chain variable region
```

```
<400> SEQUENCE: 65

Asp Ile Gln Met Thr Gln Ser Pro Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 66
<211> LENGTH: 106
<212> TYPE: PRT
<213> ORGANISM: Artificial sequence
<220> FEATURE:
<223> OTHER INFORMATION: Humanised light chain variable region

<400> SEQUENCE: 66

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 67
<211> LENGTH: 106
<212> TYPE: PRT
<213> ORGANISM: Artificial sequence
<220> FEATURE:
<223> OTHER INFORMATION: Humanised light chain variable region

<400> SEQUENCE: 67

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80
```

-continued

Asp Phe Ala Thr Tyr Tyr Cys Gln Gln Trp Ser Ser Asn Pro Phe Thr
                85                  90                  95

Phe Gly Gln Gly Thr Lys Leu Glu Ile Lys
            100                 105

<210> SEQ ID NO 68
<211> LENGTH: 106
<212> TYPE: PRT
<213> ORGANISM: Artificial sequence
<220> FEATURE:
<223> OTHER INFORMATION: Humanised light chain variable region

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Phe Thr
                85                  90                  95

Phe Gly Gln Gly Thr Lys Val Glu Ile Lys
            100                 105

<210> SEQ ID NO 69
<211> LENGTH: 119
<212> TYPE: PRT
<213> ORGANISM: Mus musculus

<400> SEQUENCE: 69

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 70
<211> LENGTH: 119
<212> TYPE: PRT
<213> ORGANISM: Artificial sequence
<220> FEATURE:
<223> OTHER INFORMATION: Humanised heavy chain variable region -continued

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser
        115

<210> SEQ ID NO 71
<211> LENGTH: 119
<212> TYPE: PRT
<213> ORGANISM: Artificial sequence
<220> FEATURE:
<223> OTHER INFORMATION: Humanised heavy chain variable region

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Arg Leu Glu Trp Met
        35                  40                  45

Gly Tyr Ile Asn Pro Ser Arg Gly Tyr Thr Asn Tyr Asn Gln Lys Phe
    50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Artificial sequence
<220> FEATURE:
<223> OTHER INFORMATION: Humanised heavy chain variable region

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

```
Gly Tyr Ile Asn Pro Ser Arg Gly Tyr Thr Asn Tyr Asn Gln Lys Phe
        50                  55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Met Val Thr Val Ser Ser
        115

<210> SEQ ID NO 73
<211> LENGTH: 119
<212> TYPE: PRT
<213> ORGANISM: Artificial sequence
<220> FEATURE:
<223> OTHER INFORMATION: Humanised heavy chain variable region

<400> SEQUENCE: 73

Gln Val Gln Leu Val Glu Ser Gly Gly Gly Leu Val Lys Pro Gly Gly
 1               5                  10                  15

Ser Leu Arg Leu Ser Cys Ala Ala Ser Gly Tyr Thr Phe Thr Arg Tyr
                20                  25                  30

Thr Met His Trp Ile Arg Gln Ala Pro Gly Lys Gly Leu Glu Trp Val
            35                  40                  45

Ser Tyr Ile Asn Pro Ser Arg Gly Tyr Thr Asn Tyr Asn Gln Lys Phe
        50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 74
<211> LENGTH: 119
<212> TYPE: PRT
<213> ORGANISM: Artificial sequence
<220> FEATURE:
<223> OTHER INFORMATION: Humanised heavy chain variable region

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Arg Tyr
                20                  25                  30

Thr Met His Trp Val Arg Gln Ala Pro Gly Lys Gly Leu Glu Trp Val
            35                  40                  45

Ser Tyr Ile Asn Pro Ser Arg Gly Tyr Thr Asn Tyr Asn Gln Lys Phe
        50                  55                  60

Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Lys Tyr Tyr Asp Asp His Tyr Cys Leu Asp Tyr Trp Gly Gln Gly
              100                 105                 110

Thr Leu Val Thr Val Ser Ser
        115

<210> SEQ ID NO 75
<211> LENGTH: 490
<212> TYPE: PRT
<213> ORGANISM: Artificial sequence
<220> FEATURE:
<223> OTHER INFORMATION: ROR1xCD3 bispecific antibody amino acid
      sequence

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Glu His
                20                  25                  30

Asn Met Ala Trp Val Arg Gln Ala Pro Gly Lys Gly Leu Glu Trp Val
            35                  40                  45

Ala Thr Ile Ser Asp Asp Gly Arg Asn Thr Tyr Tyr Arg Asp Ser Met
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ser His Arg Tyr Asn Leu Phe Asp Ser Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
130                 135                 140

Ala Ser Val Gly Asp Arg Val Thr Ile Thr Cys Lys Ala Ser Gln Asn
145                 150                 155                 160

Ile Asp Arg Tyr Leu Asn Trp Tyr Gln Gln Lys Pro Gly Lys Ala Pro
                165                 170                 175

Lys Arg Leu Ile Tyr Asn Thr Asn Lys Leu Gln Thr Gly Val Pro Ser
            180                 185                 190

Arg Phe Ser Gly Ser Gly Ser Gly Thr Glu Phe Thr Leu Thr Ile Ser
        195                 200                 205

Ser Leu Gln Pro Glu Asp Phe Ala Thr Tyr Tyr Cys Leu Gln Tyr Asn
    210                 215                 220

Ser Leu Pro Leu Thr Phe Gly Gln Gly Thr Lys Leu Glu Ile Lys Ser
225                 230                 235                 240

Gly Ser Gly Gly Gly Ser Gln Val Gln Leu Val Gln Ser Gly Ala
                245                 250                 255

Glu Val Lys Lys Pro Gly Ser Ser Val Lys Val Ser Cys Lys Ala Ser
            260                 265                 270

Gly Tyr Thr Phe Thr Arg Tyr Thr Met His Trp Val Arg Gln Ala Pro
        275                 280                 285

Gly Gln Gly Leu Glu Trp Met Gly Tyr Ile Asn Pro Ser Arg Gly Tyr
    290                 295                 300

Thr Asn Tyr Asn Gln Lys Phe Lys Asp Arg Val Thr Ile Thr Ala Asp
305                 310                 315                 320

```
Lys Ser Thr Ser Thr Ala Tyr Met Glu Leu Ser Ser Leu Arg Ser Glu
            325                 330                 335

Asp Thr Ala Val Tyr Tyr Cys Ala Arg Tyr Tyr Asp Asp His Tyr Cys
            340                 345                 350

Leu Asp Tyr Trp Gly Gln Gly Thr Met Val Thr Val Ser Ser Val Glu
            355                 360                 365

Gly Gly Ser Gly Gly Ser Gly Gly Ser Gly Gly Val Asp
            370                 375                 380

Asp Ile Gln Met Thr Gln Ser Pro Ser Ser Leu Ser Ala Ser Val Gly
385                 390                 395                 400

Asp Arg Val Thr Ile Thr Cys Ser Ala Ser Ser Val Ser Tyr Met
            405                 410                 415

Asn Trp Tyr Gln Gln Lys Pro Gly Lys Ala Pro Lys Arg Leu Ile Tyr
            420                 425                 430

Asp Thr Ser Lys Leu Ala Ser Gly Val Pro Ser Arg Phe Ser Gly Ser
            435                 440                 445

Gly Ser Gly Thr Glu Phe Thr Leu Thr Ile Ser Ser Leu Gln Pro Glu
            450                 455                 460

Asp Phe Ala Thr Tyr Tyr Cys Gln Gln Trp Ser Ser Asn Pro Phe Thr
465                 470                 475                 480

Phe Gly Gln Gly Thr Lys Val Glu Ile Lys
            485                 490

<210> SEQ ID NO 76
<211> LENGTH: 496
<212> TYPE: PRT
<213> ORGANISM: Artificial sequence
<220> FEATURE:
<223> OTHER INFORMATION: ROR1xCD3 bispecific antibody amino acid
      sequence with an N-terminal hexa-histidine tag

<400> SEQUENCE: 76

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Glu His
            20                  25                  30

Asn Met Ala Trp Val Arg Gln Ala Pro Gly Lys Gly Leu Glu Trp Val
            35                  40                  45

Ala Thr Ile Ser Asp Asp Gly Arg Asn Thr Tyr Tyr Arg Asp Ser Met
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Ser His Arg Tyr Asn Leu Phe Asp Ser Trp Gly Gln Gly Thr Met
            100                 105                 110

Val Thr Val Ser Ser Gly Gly Gly Gly Ser Gly Gly Gly Gly Ser Gly
            115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Lys Ala Ser Gln Asn
145                 150                 155                 160

Ile Asp Arg Tyr Leu Asn Trp Tyr Gln Gln Lys Pro Gly Lys Ala Pro
            165                 170                 175
```

```
Lys Arg Leu Ile Tyr Asn Thr Asn Lys Leu Gln Thr Gly Val Pro Ser
            180                 185                 190
Arg Phe Ser Gly Ser Gly Ser Gly Thr Glu Phe Thr Leu Thr Ile Ser
        195                 200                 205
Ser Leu Gln Pro Glu Asp Phe Ala Thr Tyr Tyr Cys Leu Gln Tyr Asn
    210                 215                 220
Ser Leu Pro Leu Thr Phe Gly Gln Gly Thr Lys Leu Glu Ile Lys Ser
225                 230                 235                 240
Gly Ser Gly Gly Gly Gly Ser Gln Val Gln Leu Val Gln Ser Gly Ala
            245                 250                 255
Glu Val Lys Lys Pro Gly Ser Ser Val Lys Val Ser Cys Lys Ala Ser
            260                 265                 270
Gly Tyr Thr Phe Thr Arg Tyr Thr Met His Trp Val Arg Gln Ala Pro
            275                 280                 285
Gly Gln Gly Leu Glu Trp Met Gly Tyr Ile Asn Pro Ser Arg Gly Tyr
    290                 295                 300
Thr Asn Tyr Asn Gln Lys Phe Lys Asp Arg Val Thr Ile Thr Ala Asp
305                 310                 315                 320
Lys Ser Thr Ser Thr Ala Tyr Met Glu Leu Ser Ser Leu Arg Ser Glu
            325                 330                 335
Asp Thr Ala Val Tyr Tyr Cys Ala Arg Tyr Tyr Asp Asp His Tyr Cys
            340                 345                 350
Leu Asp Tyr Trp Gly Gln Gly Thr Met Val Thr Val Ser Ser Val Glu
            355                 360                 365
Gly Gly Ser Gly Gly Ser Gly Gly Ser Gly Gly Ser Gly Gly Val Asp
        370                 375                 380
Asp Ile Gln Met Thr Gln Ser Pro Ser Ser Leu Ser Ala Ser Val Gly
385                 390                 395                 400
Asp Arg Val Thr Ile Thr Cys Ser Ala Ser Ser Ser Val Ser Tyr Met
            405                 410                 415
Asn Trp Tyr Gln Gln Lys Pro Gly Lys Ala Pro Lys Arg Leu Ile Tyr
            420                 425                 430
Asp Thr Ser Lys Leu Ala Ser Gly Val Pro Ser Arg Phe Ser Gly Ser
            435                 440                 445
Gly Ser Gly Thr Glu Phe Thr Leu Thr Ile Ser Ser Leu Gln Pro Glu
    450                 455                 460
Asp Phe Ala Thr Tyr Tyr Cys Gln Gln Trp Ser Ser Asn Pro Phe Thr
465                 470                 475                 480
Phe Gly Gln Gly Thr Lys Val Glu Ile Lys His His His His His His
            485                 490                 495
```

BISPECIFIC ANTIBODIES TO ROR1 AND CD3

The invention relates to bispecific antibodies which selectively bind to Receptor Tyrosine Kinase Like Orphan Receptor 1 (ROR1) and the CD3 subunit of the T-Cell Receptor (TCR).

BACKGROUND OF THE INVENTION

Receptor Tyrosine Kinase Like Orphan Receptor 1 (ROR1) (also known as Neurotrophic Tyrosine Kinase, Receptor-Related 1, NTRKR1) is an onco-foetal antigen expressed during embryogenesis but with limited expression on normal adult tissue. It is however expressed on a number of haematological and solid malignancies: Chronic Lymphocytic Leukaemia (CLL), Acute Lymphoblastic Leukaemia (ALL), Mantle Cell Leukaemia, Hairy Cell Leukaemia, Pancreatic cancer, Prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

As such, ROR1 is an attractive therapeutic target. Furthermore, a need remains for agents that can be used to treat the aforementioned cancers.

SUMMARY OF THE INVENTION

A first aspect of the invention relates to a bispecific antibody molecule comprising a first antigen binding domain which selectively binds to Receptor Tyrosine Kinase Like Orphan Receptor 1 (ROR1), wherein the first antigen binding domain binds to an epitope of ROR1 comprising amino acid Gln-261; and
a second antigen binding domain which selectively binds to the CD3 subunit of the T-Cell Receptor (TCR).

In a first embodiment, the first antigen binding domain comprises a light chain variable domain and a heavy chain variable domain, wherein the light chain variable domain comprises a light chain complementarity determining region (LCDR)1, an LCDR2 and an LCDR3, wherein LCDR1 comprises the amino acid sequence set forth in SEQ ID NO: 16; LCDR2 comprises the amino acid sequence set forth in SEQ ID NO: 18; and LCDR3 comprises the amino acid sequence set forth in SEQ ID NO: 20; and wherein the heavy chain variable domain comprises a heavy chain complementarity determining region (HCDR)1, an HCDR2 and an HCDR3, wherein HCDR1 comprises the amino acid sequence set forth in SEQ ID NO: 23; HCDR2 comprises the amino acid sequence set forth in SEQ ID NO: 25; and HCDR3 comprises the amino acid sequence set forth in SEQ ID NO: 57; wherein the sequence of each complementarity determining region may differ from the given sequence at up to two amino acid positions.

The present invention also relates to a composition comprising an effective amount of the above antibody in combination with a pharmaceutically acceptable carrier.

Furthermore, the present invention relates to an isolated nucleic acid molecule encoding the above antibody.

Additionally, the present invention relates to a method for treating cancer in a subject, comprising administering to the subject a therapeutically effective amount of the antibody or a nucleic acid encoding the antibody, thereby treating cancer. The present invention also relates to the antibody or nucleic acid for use in the treatment of cancer. Furthermore, the present invention relates to the use of the antibody or the nucleic acid in the preparation of a medicament for the treatment of cancer.

The disclosed monoclonal antibodies specifically bind to a ROR1 polypeptide. In additional embodiments, the monoclonal antibodies specifically bind a ROR1 polypeptide with an equilibrium constant ($K_D$) of about $6 \times 10^{-9}$ M or less. In some embodiments, the monoclonal antibodies specifically bind a ROR1 polypeptide with a $K_D$ of about $1.6 \times 10^{-9}$ M or less, about $2 \times 10^{-9}$ M or less, about $3 \times 10^{-9}$ M or less, about $4 \times 10^{-9}$ M or less or about $5 \times 10^{-9}$ M or less.

DETAILED DESCRIPTION

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs.

Administration: The introduction of a composition into a subject by a chosen route. Administration can be local or systemic. For example, if the chosen route is intravenous, the composition is administered by introducing the composition into a vein of the subject. In some examples a disclosed antibody is administered to a subject.

Agent: Any substance or any combination of substances that is useful for achieving an end or result; for example, a substance or combination of substances useful for preventing or treating cancer. Agents include, and are not limited to, proteins, nucleic acid molecules, compounds, small molecules, organic compounds, inorganic compounds, or other molecules of interest. An agent can include a therapeutic agent (such as an anti-viral agent), a diagnostic agent or a pharmaceutical agent. In some embodiments, the agent is a polypeptide agent (such as a neutralizing antibody). The skilled artisan will understand that particular agents may be useful to achieve more than one result.

Amino acid substitution: The replacement of one amino acid in a peptide with a different amino acid.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European Patent Publication EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as a ROR1 polypeptide, or an immunogenic fragment thereof. Immunoglobulin genes include the kappa, lambda, alpha, gamma, delta, epsilon and mu constant region genes, as well as the myriad immunoglobulin variable region genes.

Antibodies exist, for example, as intact immunoglobulins and as a number of well characterised fragments produced by digestion with various peptidases. For instance, Fabs, Fvs, scFvs that specifically bind to a ROR1 polypeptide, or fragments of this polypeptide, are specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies and heteroconjugate antibodies such as bispecific antibodies. See also, *Pierce Catalog and Handbook,* 1994-1995 (Pierce Chemical Co., Rockford, Ill.); Kuby, *Immunology,* 3$^{rd}$ Ed., W.H. Freeman & Co., New York, 1997.

Antibody fragments include, but are not limited to, the following: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

Antigen binding fragments of an antibody can be produced by the modification of whole antibodies or those synthesized de novo using recombinant DNA methodologies. In some examples, the term antibody includes the amino acid sequences of one or more of the CDRs from the antibody grafted onto a scaffold.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. The disclosed antibodies can be class switched.

Each heavy and light chain contains a constant region and a variable region, (the regions are also known as "domains"). In several embodiments, the heavy and the light chain variable domains combine to specifically bind the antigen. In additional embodiments, only the heavy chain variable domain is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). Light and heavy chain variable domains contain a "framework" region interrupted by three hypervariable regions, also called "complementarity-determining regions" or "CDRs" (see, e.g., Kabat et al., *Sequences of Proteins of Immunological Interest,* U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for antigen binding. The sequences of the framework regions of different light or heavy chains are relatively conserved within a species. The framework region of an antibody, that is the combined framework regions of the constituent light and heavy chains, serves to position and align the CDRs in three-dimensional space.

The CDRs of each chain are typically referred to as CDR1, CDR2, and CDR3 (from the N-terminus to C-terminus), and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs can also be referred to as CDR L1, CDR L2 and CDR L3, or LCDR1, LCDR2 and LCDR3. Heavy chain CDRs can be referred to as CDR H1, CDR H2 and CDR H3, or HCDR1, HCDR2 and HCDR3.

References to "$V_H$" or "VH" refer to the variable region of an immunoglobulin heavy chain, including that of an antibody fragment, such as Fv, scFv, dsFv or Fab.

References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas". In some embodiments, monoclonal antibodies can be humanized monoclonal antibodies. In some embodiments, monoclonal antibodies can be chimeric antibodies. In some examples monoclonal antibodies are isolated from a subject. The amino acid sequences of such isolated monoclonal antibodies can be determined.

A "humanised" antibody is an antibody including a human framework region and one or more CDRs from a non-human (such as a chimpanzee, mouse, rat, or synthetic) immunoglobulin. The non-human antibody providing the CDRs is termed a "donor", and the human antibody providing the framework is termed an "acceptor". In one embodiment, all the CDRs are from the donor antibody in a humanised antibody. Constant regions need not be present, but if they are, they must be substantially identical to human antibody constant regions, such as at least about 85-90%, such as about 95% or more identical. Hence, all parts of a humanised antibody, except possibly the CDRs, are substantially identical to corresponding parts of natural human antibody sequences. A "humanised antibody" can include a humanised light chain and a humanised heavy chain. A humanised antibody binds to the same antigen as the donor antibody that provides the CDRs. The acceptor framework of a humanised antibody may have a limited number of substitutions by amino acids taken from the donor framework. Humanised or other monoclonal antibodies can have additional conservative amino acid substitutions which have substantially no effect on antigen binding or other immunoglobulin functions. Humanised immunoglobulins can be constructed by means of genetic engineering (for example, see U.S. Pat. No. 5,585,089). Preferably, the antibodies of the present invention are humanised.

A "chimeric" antibody is an antibody which includes sequences from two different antibodies, which typically are of different species. For example, a chimeric antibody may comprise heavy and light chain variable regions derived from a first species and heavy and light chain constant regions derived from a second species. The variable and constant regions of the light chain may be derived from a first species while the variable region of the heavy chain may be derived from the first species and the constant region of the heavy chain is derived from a second species.

A "neutralizing antibody" is an antibody which reduces effect of a virus, bacteria or tumour for example, by binding to a specific antigen on the virus, bacteria or tumour. In some examples, an antibody that is specific for a ROR1 neutralises the effect of the tumour.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. Antigens can include peptides derived from a pathogen of interest or from a cancerous cell. Exemplary pathogens include bacteria, fungi, viruses and parasites. In some embodiments, an antigen is derived from a cancerous cell such as a haematological cancerous cell (chronic lymphocytic leukaemia—CLL, acute lymphoblastic leukaemia, mantle cell lymphoma) or a solid malignancy (breast, pancreatic, melanoma). In some embodiments, the antigen is a ROR1 polypeptide or antigenic fragment thereof.

A "target epitope" is a specific epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody.

Binding affinity: Affinity of an antibody or antigen binding fragment thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, at least about $5.0\times10^{-8}$ M, or at least about $1\times10^{-9}$ M.

Conjugate: A complex of two molecules linked together, for example, linked together by a covalent bond. In one embodiment, an antibody is linked to an effector molecule; for example, an antibody that specifically binds to a ROR1 polypeptide, covalently linked to an effector molecule or to a toxin. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules." In one embodiment, an antibody linked to an effector molecule is further joined to a lipid or other molecule to a protein or peptide to increase its half-life in the body.

Control: A reference standard. In some embodiments, the control is a sample obtained from a healthy patient. In other embodiments, the control is a tissue sample obtained from a patient diagnosed with cancer that serves as a positive control. In still other embodiments, the control is a historical control or standard reference value or range of values (such as a previously tested control sample, such as a group of infected patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In particular embodiments of the invention, the antibody or fragment thereof can be labelled with a detectable marker.

Detecting: To identify the existence, presence, or fact of something. General methods of detecting are known to the skilled artisan (see, for example, U.S. Pat. No. 7,635,476) and may be supplemented with the protocols and reagents disclosed herein.

For example, included herein are methods of detecting a cell that expresses a ROR1 polypeptide in a subject.

Epitope: An antigenic determinant. These are particular chemical groups or peptide sequences on a molecule that are antigenic, i.e. that elicit a specific immune response.

An antibody specifically binds a particular antigenic epitope on a polypeptide. In some examples a disclosed antibody specifically binds to an epitope on the surface of ROR1.

Framework Region: Amino acid sequences interposed between CDRs. The term includes variable light and variable heavy framework regions. The framework regions serve to hold the CDRs in an appropriate orientation for antigen binding.

Fc polypeptide: The polypeptide comprising the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not comprise the tailpiece, and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to comprise residues C226 or P230 to its carboxyl-terminus, wherein the numbering is according to the EU index. For IgA, the Fc region comprises immunoglobulin domains Calpha2 and Calpha3 (Cα2 and Cα3) and the lower part of the hinge between Calpha1 (Cα1) and Cα2. Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose Fc region as defined above; for example IgG and IgA Fc regions as defined herein must comprise the majority of the sequence encoding $CH_2$ and the majority of the sequence encoding $CH_3$. Thus, the $CH_2$ domain on its own, or the $CH_3$ domain on its own, are not considered Fc region. The Fc region may refer to this region in isolation, or this region in the context of an Fc fusion polypeptide.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Inhibiting or treating a disease: Inhibiting the full development of a disease or condition, for example, in a subject who is at risk for cancer. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in size of the tumour/cancer, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a cell, for example a B-cell, a nucleic acid, peptide, protein, heavy chain domain or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids. In some examples an antibody, such as an antibody specific for a ROR1 polypeptide can be isolated, for example isolated from a subject with a tumour expressing ROR1.

$K_d$: The dissociation constant for a given interaction, such as a polypeptide ligand interaction or an antibody antigen interaction. For example, for the bimolecular interaction of an antibody (such as any of the antibodies disclosed herein) and an antigen (such as a ROR1 polypeptide) it is the concentration of the individual components of the bimolecular interaction divided by the concentration of the complex.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In some examples, a disclosed antibody is labeled.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T." Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

ClustalW is a program that aligns three or more sequences in a computationally efficient manner. Aligning multiple sequences highlights areas of similarity which may be associated with specific features that have been more highly conserved than other regions. Thus, this program can classify sequences for phylogenetic analysis, which aims to model the substitutions that have occurred over evolution and derive the evolutionary relationships between sequences. The ClustalW multiple sequence alignment web form is available on the internet from EMBL-EBI (ebi.ac.uk/Tools/msa/clustalw2/), see also Larkin et al., *Bioinformatics* 2007 23(21): 2947-2948.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids, which include, but are not limited to, water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. In some examples a pharmaceutical agent includes one or more of the disclosed antibodies.

Polypeptide: Any chain of amino acids, regardless of length or post-translational modification (e.g., glycosylation or phosphorylation). In one embodiment, the polypeptide is a ROR1 polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal end. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity.

Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of polypeptide sequences for comparison are well known in the art. Various programs and alignment algorithms may be used as described above. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet (along with a description of how to determine sequence identity using this program).

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided.

Nucleic acids that "selectively hybridise" or "selectively bind" do so under moderately or highly stringent conditions that excludes non-related nucleotide sequences. In nucleic acid hybridisation reactions, the conditions used to achieve a particular level of stringency will vary, depending on the nature of the nucleic acids being hybridised. For example, the length, degree of complementarity, nucleotide sequence composition (for example, GC v. AT content), and nucleic acid type (for example, RNA versus DNA) of the hybridising regions of the nucleic acids can be considered in selecting hybridisation conditions. An additional consideration is whether one of the nucleic acids is immobilised, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., Molecular Cloning: A Laboratory Manual, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a tumour, for example ROR1) and do not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-7}$ Molar, such as less than about $10^{-7}$ Molar, $10^{-8}$ Molar, $10^{-9}$, or even less than about $10^{-10}$ Molar.

Therapeutic agent: Used in a generic sense, it includes treating agents, prophylactic agents, and replacement agents.

Therapeutically effective amount or effective amount: A quantity of a specific substance, such as a disclosed antibody, sufficient to achieve a desired effect in a subject being treated. For instance, this can be the amount necessary to inhibit tumour growth. In several embodiments, a therapeutically effective amount is the amount necessary to reduce a symptom of the disease. When administered to a subject, a dosage will generally be used that will achieve target tissue concentrations that has been shown to achieve a desired in vitro effect.

Vector: A nucleic acid molecule may be introduced into a host cell by a vector, thereby producing a transformed host cell. A vector may include nucleic acid sequences that permit it to replicate in a host cell, such as an origin of replication. A vector may also include one or more selectable marker genes and other genetic elements known in the art.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Bispecific Antibodies that Specifically Bind to ROR1 and CD3

Clinically useful antibodies that specifically bind ROR1 and CD3 are disclosed herein.

In some embodiments the antibody specifically binds a ROR1 polypeptide with an equilibrium constant ($K_d$) of about $6\times10^{-9}$ M or less. In some embodiments, the antibody specifically binds a ROR1 polypeptide with a $K_d$ of about $1.6\times10^{-9}$ M or less, about $2\times10^{-9}$ M or less, about $3\times10^{-9}$ M or less, about $4\times10^{-9}$ M or less or about $5\times10^{-9}$ M or less.

The antibodies can be of any isotype. The antibodies can be, for example, an IgM or an IgG antibody, such as $IgG_1$ or an $IgG_2$. The class of an antibody that specifically binds ROR1 can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds ROR1 that was originally IgM may be class switched to an IgG. Class switching can be used to convert one IgG subclass to another, such as from $IgG_1$ to $IgG_2$.

The antibody disclosed herein can be a rat antibody, and can include a rat framework region. In some preferred embodiments, the antibody is humanised, and thus include one or more human framework regions. In some embodiments, the antibody disclosed herein is a chimeric antibody. In some embodiments, the antibody includes rat and human regions.

The antibody can specifically bind a ROR1 polypeptide. Preferably, the antibody can specifically bind a human ROR1 polypeptide. The antibody preferably comprises a heavy chain and a light chain and preferably each VH and VL is composed of three CDRs and four FWRs, arranged from amino-terminus to carboxy-terminus in the following order: FWR1, CDR1, FWR2, CDR2, FWR3, CDR3, FWR4 as described above.

In a first embodiment, the first antigen binding domain which selectively binds to Receptor Tyrosine Kinase Like Orphan Receptor 1 (ROR1) comprises a light chain variable domain and a heavy chain variable domain, wherein the light chain variable domain comprises a light chain complementarity determining region (LCDR)1, an LCDR2 and an LCDR3, wherein LCDR1 comprises the amino acid sequence set forth in SEQ ID NO: 16; LCDR2 comprises the amino acid sequence set forth in SEQ ID NO: 18; and LCDR3 comprises the amino acid sequence set forth in SEQ ID NO: 20; and wherein the heavy chain variable domain comprises a heavy chain complementarity determining region (HCDR)1, an HCDR2 and an HCDR3, wherein HCDR1 comprises the amino acid sequence set forth in SEQ ID NO: 23; HCDR2 comprises the amino acid sequence set forth in SEQ ID NO: 25; and HCDR3 comprises the amino acid sequence set forth in SEQ ID NO: 57; wherein the sequence of each complementarity determining region may differ from the given sequence at up to two amino acid positions.

The antibody specifically binds to a ROR1 polypeptide and specifically binds to CD3. The first and/or second antigen binding domain may be a monoclonal antibody or an antigen binding fragment thereof. In particular embodiments both the first and second antigen binding domains are a monoclonal antibody or an antigen binding fragment thereof.

As indicated above, the sequence of each CDR may differ from the given sequence at up to two amino acid positions. This means that the CDR may contain one or two amino acid substitutions compared to the given sequence. However, if one or more of the CDRs does contain amino acid substitutions, the antibody can still selectively bind to ROR1. Preferably, the amino acid substitutions are conservative substitutions.

Preferably, the sequence of each CDR may differ from the given sequence at one amino acid position. This means that the CDR may contain one amino acid substitution compared to the given sequence. Preferably, the amino acid substitution is a conservative substitution.

In some embodiments, heavy chain complementarity determining region 3 (HCDR3) comprises an amino acid sequence selected from any of the sequences set forth in SEQ ID NOs: 27, 36, 44 and 49. Preferably, HCDR3 comprises an amino acid sequence selected from any of the sequences set forth in SEQ ID NOs: 36, 44 and 49.

The first antigen binding domain may have a light chain variable domain which comprises a Light Chain Framework Region (LCFR)1 comprising the amino acid sequence as set forth as one of SEQ ID NOs: 15, 29, 50 and 53; an LCFR2 comprising the amino acid sequence as set forth as one of SEQ ID NOs: 17, 30, 38 and 46; an LCFR3 comprising the amino acid sequence as set forth as one of SEQ ID NOs: 19, 31, 39, 47 and 54; and an LCFR4 comprising the amino acid sequence as set forth as one of SEQ ID NOs: 21, 32 and 40.

Preferably, the first antigen binding domain has a light chain variable domain which comprises an LCFR1 comprising the amino acid sequence as set forth as one of SEQ ID NOs: 29, 50 and 53; an LCFR2 comprising the amino acid sequence as set forth as one of SEQ ID NOs: 30, 38 and 46; an LCFR3 comprising the amino acid sequence as set forth as one of SEQ ID NOs: 31, 39, 47 and 54; and an LCFR4 comprising the amino acid sequence as set forth as one of SEQ ID NOs: 32 and 40.

The first antigen binding domain may have a heavy chain variable domain which comprises a Heavy Chain Framework Region (HCFR)1 comprising the amino acid sequence as set forth as one of SEQ ID NOs: 22, 33, 41 and 55; an HCFR2 comprising the amino acid sequence as set forth as one of SEQ ID NOs: 24, 34, 42 and 51; an HCFR3 comprising the amino acid sequence as set forth as one of SEQ ID NOs: 26, 35, 43, 48, 52 and 56; and an HCFR4 comprising the amino acid sequence as set forth as one of SEQ ID NOs: 28, 37 and 45.

Preferably, the first antigen binding domain may have a heavy chain variable domain which comprises an HCFR1 comprising the amino acid sequence as set forth as one of SEQ ID NOs: 33, 41 and 55; an HCFR2 comprising the amino acid sequence as set forth as one of SEQ ID NOs: 34, 42 and 51; an HCFR3 comprising the amino acid sequence as set forth as one of SEQ ID NOs: 35, 43, 48, 52 and 56; and an HCFR4 comprising the amino acid sequence as set forth as one of SEQ ID NOs: 37 and 45.

As indicated below, the sequence of each framework region referred to above may differ from the given sequence. For example, it may differ at up to 10 amino acid positions, although it is preferred that fewer than 10 amino acid substitutions are present so that there may be up to 9, 8, 7, 6, 5, 4, 3, 2 or 1 amino acid substitutions. Alternatively, each framework region may comprise an amino acid sequence which is at least 90%, 91%, 92%, 93%, 94%, 95%, 96%, 97%, 98% or 99% identical to the amino acid sequences as set forth in the sequence listing.

Preferably, the light chain variable domain comprises the amino acid sequence as set forth as one of SEQ ID NOs: 3, 4, 5, 6, 7 and 8. More preferably, the light chain variable domain comprises the amino acid sequence as set forth as one of SEQ ID NOs: 4, 5, 6, 7 and 8.

Preferably, the heavy chain variable domain comprises the amino acid sequence as set forth as one of SEQ ID NOs: 9, 10, 11, 12, 13 and 14. More preferably, the heavy chain variable domain comprises the amino acid sequence as set forth as one of SEQ ID NOs: 10, 11, 12, 13 and 14.

SEQ ID NOs: 4, 5, 6, 7 and 8 are humanised light chain variable regions. SEQ ID NOs: 10, 11, 12, 13 and 14 are humanised light chain variable regions. The inventors tried all combinations of these light and heavy chain regions resulting in 25 different constructs.

Therefore, in some embodiments, the light chain variable domain comprises the amino acid sequence as set forth as SEQ ID NO: 4 and the heavy chain variable domain comprises the amino acid sequence as set forth as one of SEQ ID NOs: 10, 11, 12, 13 and 14. In a particular embodiment, the light chain variable domain comprises the amino acid sequence as set forth as SEQ ID NO: 4 and the heavy chain variable domain comprises the amino acid sequence as set forth as one of SEQ ID NOs: 10, 12 and 13.

In other embodiments, the light chain variable domain comprises the amino acid sequence as set forth as SEQ ID NO: 5 and the heavy chain variable domain comprises the amino acid sequence as set forth as one of SEQ ID NOs: 10, 11, 12, 13 and 14.

In further embodiments, the light chain variable domain comprises the amino acid sequence as set forth as SEQ ID NO: 6 and the heavy chain variable domain comprises the amino acid sequence as set forth as one of SEQ ID NOs: 10, 11, 12, 13 and 14.

In alternative embodiments, the light chain variable domain comprises the amino acid sequence as set forth as SEQ ID NO: 7 and the heavy chain variable domain comprises the amino acid sequence as set forth as one of SEQ ID NOs: 10, 11, 12, 13 and 14.

In various embodiments, the light chain variable domain comprises the amino acid sequence as set forth as SEQ ID NO: 8 and the heavy chain variable domain comprises the amino acid sequence as set forth as one of SEQ ID NOs: 10, 11, 12, 13 and 14.

Similarly, in some embodiments, the heavy chain variable domain comprises the amino acid sequence as set forth as SEQ ID NO: 10 and the light chain variable domain comprises the amino acid sequence as set forth as one of SEQ ID NOs: 4, 5, 6, 7 and 8.

In other embodiments, the heavy chain variable domain comprises the amino acid sequence as set forth as SEQ ID NO: 11 and the light chain variable domain comprises the amino acid sequence as set forth as one of SEQ ID NOs: 4, 5, 6, 7 and 8.

In further embodiments, the heavy chain variable domain comprises the amino acid sequence as set forth as SEQ ID NO: 12 and the light chain variable domain comprises the amino acid sequence as set forth as one of SEQ ID NOs: 4, 5, 6, 7 and 8.

In alternative embodiments, the heavy chain variable domain comprises the amino acid sequence as set forth as SEQ ID NO: 13 and the light chain variable domain comprises the amino acid sequence as set forth as one of SEQ ID NOs: 4, 5, 6, 7 and 8.

In various embodiments, the heavy chain variable domain comprises the amino acid sequence as set forth as SEQ ID NO: 14 and the light chain variable domain comprises the amino acid sequence as set forth as one of SEQ ID NOs: 4, 5, 6, 7 and 8.

In particular embodiments,
(a) the light chain variable domain comprises the amino acid sequence as set forth as SEQ ID NO: 3 and the heavy chain variable domain comprises the amino acid sequence as set forth as SEQ ID NO: 9;
(b) the light chain variable domain comprises the amino acid sequence as set forth as SEQ ID NO: 4 and the heavy chain variable domain comprises the amino acid sequence as set forth as SEQ ID NO: 10;
(c) the light chain variable domain comprises the amino acid sequence as set forth as SEQ ID NO: 5 and the heavy chain variable domain comprises the amino acid sequence as set forth as SEQ ID NO: 11;
(d) the light chain variable domain comprises the amino acid sequence as set forth as SEQ ID NO: 6 and the heavy chain variable domain comprises the amino acid sequence as set forth as SEQ ID NO: 12;
(e) the light chain variable domain comprises the amino acid sequence as set forth as SEQ ID NO: 7 and the heavy chain variable domain comprises the amino acid sequence as set forth as SEQ ID NO: 13; or
(f) the light chain variable domain comprises the amino acid sequence as set forth as SEQ ID NO: 8 and the heavy chain variable domain comprises the amino acid sequence as set forth as SEQ ID NO: 14.

As indicated below, the sequence of each light chain variable domain and heavy chain variable domain referred to above may differ from the given sequence. For example, the light/heavy chain variable domain may comprise a sequence which is at least 90%, 91%, 92%, 93%, 94%, 95%, 96%, 97%, 98% or 99% identical to the amino acid sequences as set forth in the sequence listing. Alternatively, the light/heavy chain variable domain sequence may differ at up to 10 amino acid positions, although it is preferred that fewer than 10 amino acid substitutions are present so that there may be up to 9, 8, 7, 6, 5, 4, 3, 2 or 1 amino acid substitutions.

As referred to above, in some embodiments, the Light Chain Framework Regions, the Heavy Chain Framework Regions, the Light Chain Variable Domains and the Heavy Chain Variable Domains comprise an amino acid sequence at least 90%, 91%, 92%, 93%, 94%, 95%, 96%, 97%, 98% or 99% identical to the amino acid sequences as set forth above. For example, the Light Chain Framework Regions, the Heavy Chain Framework Regions, the Light Chain Variable Domains and the Heavy Chain Variable Domains may include at most 10, at most 9, at most 8, at most 7, at most 6, at most 5, at most 4, at most 3, at most two or at most one amino acid substitutions in the amino acid sequences as set forth above. Where there is variation in the sequences of the Light Chain Variable Domain and the Heavy Chain Variable Domain, any amino acid substitutions are preferably not in the CDRs. In particular, the Light Chain Framework Regions and/or the Heavy Chain Framework Regions of the antibodies described above may comprise an amino acid sequence at least 90%, 91%, 92%, 93%, 94%, 95%, 96%, 97%, 98% or 99% identical to the amino acid sequences as set forth above. Further, the Light Chain Framework Regions and/or the Heavy Chain Framework Regions may include at most 10, at most 9, at most 8, at most 7, at most 6, at most 5, at most 4, at most 3, at most two or at most one amino acid substitutions in the amino acid sequences as set forth above. Preferably the amino acid substitutions are conservative substitutions as described above. For example, the framework regions may comprise such substitutions in order to humanise the sequence. Preferably, the framework regions are humanised.

In a second embodiment, the first antigen binding domain which selectively binds to Receptor Tyrosine Kinase Like Orphan Receptor 1 (ROR1) comprises a light chain variable domain and a heavy chain variable domain, wherein the light chain variable domain comprises an LCDR1, an LCDR2 and an LCDR3, wherein LCDR1 comprises the amino acid sequence set forth in SEQ ID NO: 58; LCDR2 comprises the amino acid sequence set forth in SEQ ID NO: 59; and LCDR3 comprises the amino acid sequence set forth in SEQ ID NO: 20; and wherein the heavy chain variable domain comprises an HCDR1, an HCDR2 and an HCDR3, wherein HCDR1 comprises the amino acid sequence set forth in SEQ ID NO: 60; HCDR2 comprises the amino acid sequence set forth in SEQ ID NO: 61; and HCDR3 comprises the amino acid sequence set forth in SEQ ID NO: 62; wherein the sequence of each complementarity determining region may differ from the given sequence at up to two amino acid positions.

As indicated above, the sequence of each CDR may differ from the given sequence at up to two amino acid positions. This means that the CDR may contain one or two amino acid substitutions compared to the given sequence. However, if one or more of the CDRs does contain amino acid substitutions, the antibody can still selectively bind to ROR1. Preferably, the amino acid substitutions are conservative substitutions.

Preferably, the sequence of each CDR may differ from the given sequence at one amino acid position. This means that the CDR may contain one amino acid substitution compared to the given sequence. Preferably, the amino acid substitution is a conservative substitution. More preferably, the sequence of each CDR does not differ from the given sequence.

The antibody specifically binds to a ROR1 polypeptide and specifically binds to CD3. The first and/or second antigen binding domain may be a monoclonal antibody or an antigen binding fragment thereof. In particular embodiments both the first and second antigen binding domains are a monoclonal antibody or an antigen binding fragment thereof.

Preferably, the light chain variable domain comprises the amino acid sequence as set forth as one of SEQ ID NOs: 3, 4, 5, 6, 7 and 8. More preferably, the light chain variable domain comprises the amino acid sequence as set forth as one of SEQ ID NOs: 4, 5, 6, 7 and 8.

Preferably, the heavy chain variable domain comprises the amino acid sequence as set forth as one of SEQ ID NOs: 9, 10, 11, 12, 13 and 14. More preferably, the heavy chain variable domain comprises the amino acid sequence as set forth as one of SEQ ID NOs: 10, 11, 12, 13 and 14.

As stated above with regard to the first embodiment, the inventors tried all combinations of the light chain variable domains (SEQ ID NOs: 4, 5, 6, 7 and 8) and heavy chain variable domains (SEQ ID NOs: 10, 11, 12, 13 and 14) resulting in 25 different constructs. Therefore, the description above relating to the combinations of these sequences is also applicable to the second embodiment referred to above.

In particular embodiments,
(a) the light chain variable domain comprises the amino acid sequence as set forth as SEQ ID NO: 3 and the heavy chain variable domain comprises the amino acid sequence as set forth as SEQ ID NO: 9;
(b) the light chain variable domain comprises the amino acid sequence as set forth as SEQ ID NO: 4 and the heavy chain variable domain comprises the amino acid sequence as set forth as SEQ ID NO: 10;
(c) the light chain variable domain comprises the amino acid sequence as set forth as SEQ ID NO: 5 and the heavy chain variable domain comprises the amino acid sequence as set forth as SEQ ID NO: 11;
(d) the light chain variable domain comprises the amino acid sequence as set forth as SEQ ID NO: 6 and the heavy chain variable domain comprises the amino acid sequence as set forth as SEQ ID NO: 12;
(e) the light chain variable domain comprises the amino acid sequence as set forth as SEQ ID NO: 7 and the heavy chain variable domain comprises the amino acid sequence as set forth as SEQ ID NO: 13; or
(f) the light chain variable domain comprises the amino acid sequence as set forth as SEQ ID NO: 8 and the heavy chain variable domain comprises the amino acid sequence as set forth as SEQ ID NO: 14.

The sequence of each light chain variable domain and heavy chain variable domain referred to above may differ from the given sequence. For example, the light/heavy chain variable domain may comprise a sequence which is at least 90%, 91%, 92%, 93%, 94%, 95%, 96%, 97%, 98% or 99% identical to the amino acid sequences as set forth in the sequence listing. Alternatively, the light/heavy chain variable domain sequence may differ at up to 10 amino acid positions, although it is preferred that fewer than 10 amino acid substitutions are present so that there may be up to 9, 8, 7, 6, 5, 4, 3, 2 or 1 amino acid substitutions.

For all the embodiments described above, one skilled in the art will be aware that any substitutions will retain critical amino acid residues necessary for correct folding and stabilizing between the $V_H$ and the $V_L$ regions, and will retain the charge characteristics of the residues in order to preserve the low pI and low toxicity of the antibodies. Thus, one of skill in the art can readily review the sequences shown above, identify a conservative substitution, and produce the conservative variant using well-known molecular techniques.

Epitope mapping has been carried out for the antigen binding domains discussed above. It has been found that residue Gln-261 of human ROR1 is essential for the antigen binding domain. Therefore, there is also provided an antigen binding domain that binds to an epitope of ROR1, wherein the epitope comprises amino acid Gln-261.

The second antigen binding domain which selectively binds to the CD3 subunit of the T-Cell Receptor (TCR) can be any suitable antigen binding domain and such binding domains are well known to those skilled in the art. For example, CD3 monoclonal antibodies can be obtained from ThermoFisher Scientific. Further, bispecific antibodies which bind to a tumour antigen and CD3 are also known in the art, for example, as described in Baeuerle and Reinhardt (Cancer Res (2009); 69(12): 4941-4944), Chames and Baty (MAbs. (2009); 1(6): 539-547) and Hoffman et al. (Int. J. Cancer (2005) 115, 98-104).

The second antigen binding domain which selectively binds to the CD3 subunit of the T-Cell Receptor (TCR) may comprise a light chain variable domain and a heavy chain variable domain, wherein the light chain variable domain comprises the amino acid sequence as set forth as one of SEQ ID NOs: 63, 64, 65, 66, 67 and 68, and wherein the heavy chain variable domain comprises the amino acid sequence as set forth as one of SEQ ID NOs: 69, 70, 71, 72, 73 and 74. Preferably, the light chain variable domain comprises the amino acid sequence as set forth as one of SEQ ID NOs: 64, 65, 66, 67 and 68, and the heavy chain variable domain comprises the amino acid sequence as set forth as one of SEQ ID NOs: 70, 71, 72, 73 and 74.

In particular embodiments of the second antigen binding domain,
(a) the light chain variable domain comprises the amino acid sequence as set forth as SEQ ID NO: 63 and the heavy chain variable domain comprises the amino acid sequence as set forth as SEQ ID NO: 69;
(b) the light chain variable domain comprises the amino acid sequence as set forth as SEQ ID NO: 64 and the heavy chain variable domain comprises the amino acid sequence as set forth as SEQ ID NO: 70;
(c) the light chain variable domain comprises the amino acid sequence as set forth as SEQ ID NO: 65 and the heavy chain variable domain comprises the amino acid sequence as set forth as SEQ ID NO: 71;
(d) the light chain variable domain comprises the amino acid sequence as set forth as SEQ ID NO: 66 and the heavy chain variable domain comprises the amino acid sequence as set forth as SEQ ID NO: 72;
(e) the light chain variable domain comprises the amino acid sequence as set forth as SEQ ID NO: 67 and the heavy chain variable domain comprises the amino acid sequence as set forth as SEQ ID NO: 73; or
(f) the light chain variable domain comprises the amino acid sequence as set forth as SEQ ID NO: 68 and the heavy chain variable domain comprises the amino acid sequence as set forth as SEQ ID NO: 74.

The sequence of each light chain variable domain and heavy chain variable domain of the second antigen binding domain referred to above may differ from the given sequence. For example, the light/heavy chain variable domain may comprise a sequence which is at least 90%, 91%, 92%, 93%, 94%, 95%, 96%, 97%, 98% or 99% identical to the amino acid sequences as set forth in the sequence listing. Alternatively, the light/heavy chain variable domain sequence may differ at up to 10 amino acid positions, although it is preferred that fewer than 10 amino acid substitutions are present so that there may be up to 9, 8, 7, 6, 5, 4, 3, 2 or 1 amino acid substitutions. Preferably, there are no substitutions present in the CDRs of the heavy/light chain.

The first antigen binding domain may have the structure of an antibody fragment such as Fab, F(ab')$_2$, and Fv which include a heavy chain and light chain variable region and are capable of binding the epitopic determinant on ROR1. Similarly, the second antigen binding domain may have the structure of an antibody fragment such as Fab, F(ab')$_2$, and Fv which include a heavy chain and light chain variable region and are capable of binding the epitopic determinant on CD3. These antibody fragments retain the ability to selectively bind with the antigen and are described above. Methods of making these fragments are known in the art (see for example, Harlow and Lane, *Antibodies: A Laboratory Manual*, Cold Spring Harbor Laboratory, New York, 1988).

In a further group of embodiments, the antigen binding domains may have the structure of an Fv antibody, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Exemplary linkers include the amino acid sequence GGGGS (SEQ ID NO. 1) and GGGGSGGGGS (SEQ ID NO. 2). Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments comprising the antigen binding domains can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

The antibody disclosed herein can be derivatized or linked to another molecule (such as another peptide or protein). In general, the antibody is derivatized such that the binding to the ROR1 polypeptide and CD3 subunit are not affected adversely by the derivatization or labelling. For example, the antibody can be functionally linked, for example, by chemical coupling, genetic fusion, noncovalent association or otherwise to one or more other molecular entities, such as another antibody, a detection agent, a pharmaceutical agent, and/or a protein or peptide that can mediate association of the antibody with another molecule (such as a streptavidin core region or a polyhistidine tag).

The bispecific antibody can be produced by cross-linking two or more antibodies (of the same type or of different types. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available, for example, from Pierce Chemical Company (Rockford, Ill.).

In particular embodiments, the ROR1 antigen binding domain may be a scFv antibody. In some embodiments, the CD3 antigen binding domain is a scFv antibody. In various embodiments, both the ROR1 antigen binding domain and the CD3 antigen binding domain are scFv antibodies. These two scFv antibodies may be covalently linked using a short peptide linker of between 5 and 20 amino acids.

In some embodiments, the bispecific antibody comprises the sequence of SEQ ID NO. 75 or 76, or a sequence having at least 90% sequence identity thereto. The sequence may have at least 91%, 92%, 93%, 94%, 95%, 96%, 97%, 98% or 99% sequence identity thereto. In some embodiments, the bispecific antibody comprises the sequence of SEQ ID NO. 75 or 76.

The antibody can be labelled with a detectable moiety or marker as described above.

The antibody can also be labelled with a radiolabeled amino acid. Examples of radiolabels include, but are not limited to, the following radioisotopes or radionucleotides: $^3$H, $^{14}$C, $^{15}$N, $^{35}$S, $^{90}$Y, $^{99}$Tc, $^{111}$In, $^{125}$I, $^{131}$I. The radiolabel may be used for both diagnostic and therapeutic purposes.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Polynucleotides and Expression

Nucleotide sequences encoding the bispecific antibody are also provided, as well as expression vectors that provide for their efficient expression in cells.

Recombinant expression of an antigen binding domain generally requires construction of an expression vector containing a polynucleotide that encodes the antibody or antibody fragment. Replicable vectors are provided including a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of an antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Nucleic acid molecules (also referred to as polynucleotides) encoding the antibodies provided herein (including, but not limited to the antigen binding domains) can readily be produced by one of skill in the art. For example, these nucleic acids can be produced using the amino acid sequences provided herein (such as the CDR sequences, heavy chain and light chain sequences), sequences available in the art (such as framework sequences), and the genetic code.

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the antigen binding domains that specifically bind a ROR1 polypeptide and CD3, can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3 SR). A wide variety of cloning methods, host cells, and in vitro amplification methodologies are well known to persons of skill.

Any of the nucleic acids encoding any of the antigen binding domains, $V_H$ and/or $V_L$, disclosed herein (or fragment thereof) can be expressed in a recombinantly engineered cell such as bacteria, plant, yeast, insect and mammalian cells. These antibodies can be expressed as individual $V_H$ and/or $V_L$ chain, or can be expressed as a fusion protein. An immunoadhesin can also be expressed. Thus, in some examples, nucleic acids encoding a $V_H$ and $V_L$, and immunoadhesin are provided. The nucleic acid sequences can optionally encode a leader sequence.

To create a single chain antibody, (scFv) the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site. To create a bispecific antibody from two scFv antibodies, the scFv DNA fragments can be operatively linked to another fragment encoding a flexible linker containing between 5 and 20 amino acids such that the two scFv sequences are expressed as a contiguous single-chain protein, with the two scFv antibodies joined by the flexible linker.

The nucleic acid encoding the $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an $IgG_1$ Fc.

It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. Once the expression vector is transferred to a host cell by conventional techniques, the transfected cells are then cultured by conventional techniques, such as to produce an antibody. Thus, host cells are provided containing a polynucleotide encoding an antigen binding domain, or a heavy or light chain thereof, or portion thereof, operably linked to a heterologous promoter. In certain embodiments for the expression of double-chained antigen binding domains, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In one embodiment, human cell lines are of use. In one embodiment, the human cell line PER.C6. (Crucell, Netherlands) can be used.

Additional cell lines which may be used as hosts for expression of recombinant antibodies include, but are not limited to, insect cells (e.g. Sf21/Sf9, Trichoplusia ni Bti-Tn5b1-4) or yeast cells (e.g. *S. cerevisiae*, *Pichia*, U.S. Pat. No. 7,326,681), plant cells (US Published Patent Application No. 20080066200); and chicken cells (PCT Publication No. WO2008142124).

The host cell can be a gram positive bacteria including, but not limited to, *Bacillus, Streptococcus, Streptomyces, Staphylococcus, Enterococcus, Lactobacillus, Lactococcus, Clostridium, Geobacillus*, and *Oceanobacillus*. Methods for expressing protein in gram positive bacteria, such as *Lactobacillus* are well known in the art, see for example, U.S. Published Patent Application No. 20100/080774. Expression vectors for *lactobacillus* are described, for example in U.S. Pat. Nos. 6,100,388, and 5,728,571. Leader sequences can be included for expression in *Lactobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

One or more DNA sequences encoding the antigen binding domains can be expressed in vitro by DNA transfer into a suitable host cell. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the isolated antibodies described herein can be achieved by operably linking the DNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antigen binding domain, labeled antigen binding domain, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding an antibody described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antigen binding domains of the present disclosure can also be constructed in whole or in part using standard peptide synthesis well known in the art.

Once expressed, the antigen binding domains and/or antibodies can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antigen binding domains and antibodies need not be 100% pure. Once purified, partially or to homogeneity as desired, if to be used therapeutically, the antibodies should be substantially free of endotoxin.

Methods for expression of antibodies and/or refolding to an appropriate active form, including single chain antibodies, from bacteria such as *E. coli* have been described and are well-known and are applicable to the antigen binding domains disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis,* 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art. Once an antibody molecule has been produced, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies or fragments thereof may be fused to heterologous polypeptide sequences (referred to herein as "tags") described above or otherwise known in the art to facilitate purification.

Compositions and Therapeutic Methods

A method for treating cancer in a subject is also disclosed, the method comprising administering to the subject a therapeutically effective amount of the disclosed antibody and/or a nucleic acid encoding the antibody, thereby treating cancer.

The disclosed antibodies can be cytotoxic to cancer cells.

Preferably, the cancer is leukaemia (such as Chronic Lymphocytic Leukaemia (CLL), Acute Lymphoblastic Leukaemia (ALL), Mantle Cell Leukaemia or Hairy Cell Leukaemia), pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

The present invention also relates to the disclosed antibody for use in the treatment of cancer. Further, the present invention also relates to use of the disclosed antibody in the manufacture of a medicament for the treatment of cancer.

Preferably, the cancer is leukaemia (such as Chronic Lymphocytic Leukaemia (CLL), Acute Lymphoblastic Leukaemia (ALL), Mantle Cell Leukaemia or Hairy Cell Leukaemia), pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma, renal cancer. Furthermore, ROR1 is expressed on a subset of cancer stem cells.

The cancer or tumour does not need to be completely eliminated for the composition to be effective. For example, the antibody can reduce the tumour by a desired amount, for example by at least 10%, at least 20%, at least 50%, at least 60%, at least 70%, at least 80%, at least 90%, at least 95%, at least 98%, or 100%, as compared to the absence of the composition.

Administration of the antibody of the present invention may result in a 5, 10, 20, 50, 75, 90, 95 or 99% depletion, i.e. reduction in malignant cells.

In another example, the subject can also be administered an effective amount of an additional agent, such as a chemotherapy agent. The methods can include administration of one or more additional agents known in the art.

A therapeutically effective amount of the antibody (or the nucleic acid encoding the antibody) will depend upon the severity of the disease and the general state of the patient's health. A therapeutically effective amount of the antibody can provide either subjective relief of a symptom(s) or an objectively identifiable improvement as noted by the clinician or other qualified observer. As noted above, these compositions can be administered in conjunction with another therapeutic agent, either simultaneously or sequentially. For any application, the antibody can be combined with chemotherapy.

Single or multiple administrations of the compositions including the antibody, that are disclosed herein, are administered depending on the dosage and frequency as required and tolerated by the patient. In any event, the composition should provide a sufficient quantity of at least one of the antibodies disclosed herein to effectively treat the patient.

The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Compositions are further disclosed that include the antibody or nucleic acid encoding the antibody in a carrier. The compositions can be prepared in unit dosage forms for administration to a subject. The amount and timing of administration are at the discretion of the treating physician to achieve the desired purposes. The antibody and/or nucleic acid can be formulated for systemic or local administration.

In one example, the antibody or nucleic acid encoding the antibody is formulated for parenteral administration, such as intravenous administration. In some embodiments, administration is intramuscular.

Active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the antibodies can be prepared by such methods as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. The reverse-phase evaporation method can be used with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described, for example, in Martin et al., J. Biol. Chem., 257:286-288 (1982) via a disulfide interchange reaction.

The compositions for administration can include a solution of the antibody dissolved in a pharmaceutically acceptable carrier, such as an aqueous carrier. A variety of aqueous carriers can be used, for example, buffered saline and the like. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs. In some embodiments, administration is intravenous.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., Colloidal Drug Delivery Systems, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody disclosed herein. Various degradable and nondegradable polymeric matrices for use in controlled drug delivery are known in the art (Langer, Accounts Chem. Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., Pharm. Res. 9:425-434, 1992; and Pec et al., J. Parent. Sci. Tech. 44(2):58-65, 1990). Alternatively, hydroxyapatite has been used as a microcarrier for controlled release of proteins (Ijntema et al., Int. J. Pharm. 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)).

A typical pharmaceutical composition for intravenous administration includes about 0.1 to 10 mg/kg of antibody per day, or 0.5 to 15 mg/kg of antibody per day. Dosages from 0.1 up to about 100 mg/kg per subject per day may be used, particularly if the agent is administered to a secluded site and not into the circulatory or lymph system, such as into a body cavity or into a lumen of an organ. Exemplary doses include 1 to 10 mg/kg, such as 2 to 8 mg/kg, such as 3 to 6 mg/kg. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.1 to 10 mg/kg or 0.5 to 15 mg/kg of body weight. Exemplary doses include 1 to 10 mg/kg, such as 2 to 8 mg/kg, such as 3 to 6 mg/kg. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a nucleic acid encoding the antibody can be administered to a subject in need thereof. One approach to administration of nucleic acids is direct immunization with plasmid DNA, such as with a mammalian expression plasmid. The nucleotide sequence encoding the antibody can be placed under the control of a promoter to increase expression of the molecule. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids to an organism. The methods include liposomal delivery of the nucleic acids.

In another approach to using nucleic acids, an antibody can also be expressed by attenuated viral hosts or vectors or bacterial vectors, which can be administered to a subject. Recombinant vaccinia virus, adeno-associated virus (AAV), herpes virus, retrovirus, cytomegalovirus, poxvirus or other viral vectors can be used to express the antibody. For example, vaccinia vectors are described in U.S. Pat. No. 4,722,848. BCG (Bacillus Calmette Guerin) provides another vector for expression of the disclosed antibodies (see Stover, *Nature* 351:456-460, 1991).

In one embodiment, a nucleic acid encoding the antibody is introduced directly into cells. For example, the nucleic acid can be loaded onto gold microspheres by standard methods and introduced into the skin by a device such as Bio-Rad's Heliosa Gene Gun. The nucleic acids can be "naked," consisting of plasmids under control of a strong promoter.

Typically, the DNA is injected into muscle, although it can also be injected directly into other sites. Dosages for injection are usually around 0.5 mg/kg to about 50 mg/kg, and typically are about 0.005 mg/kg to about 5 mg/kg (see, e.g., U.S. Pat. No. 5,589,466).

In some examples, a subject is administered the DNA encoding the antibody to provide in vivo antibody production, for example using the cellular machinery of the subject. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody can be placed under the control of a promoter to increase expression.

The following examples are provided to illustrate certain particular features and/or embodiments. These examples should not be construed to limit the disclosure to the particular features or embodiments described. The examples should be read in combination with the figures which are as follows:

FIG. 1: ROR1xCD3 mediated specific cytotoxicity against pancreatic ductal adenocarcinoma (PDAC) cell lines in a co-culture assay with unstimulated T-cells. (a) MTS assay demonstrating marked cytotoxicity against PANC-1 cell lines with ROR1xCD3 and T-cells but not with T-cells alone or with CD19xCD3. (b) Specific IL-2 and IFNγ secretion by T-cells in response to PANC-1 cells in the presence of ROR1xCD3. (c) Titration of ROR1xCD3 in co-culture assays using a panel of ROR1-positive PDAC cell lines, with ROR1xCD3 retaining its cytotoxic activity at concentrations as low as 0.1 ng/ml. Data representative of 2 independent experiments with different donor T-cells.

Figure 2:
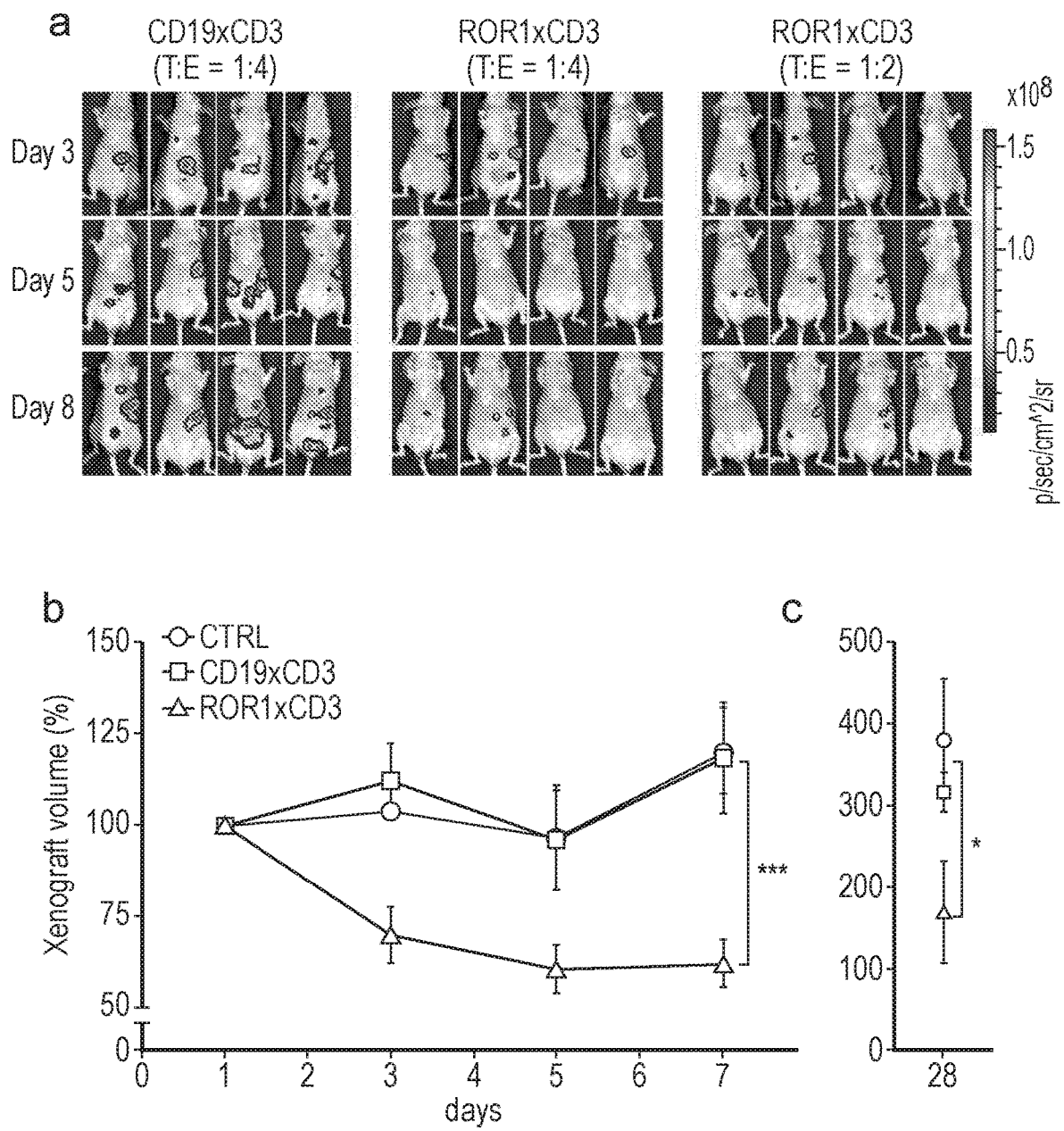

FIG. 2: In vivo assessment of ROR1xCD3. (a) Intraperitoneal Engraftment: $2 \times 10^6$ PANC-1.Luc cells/mouse were administered followed by purified human T cells injection ip ($8 \times 10^6$ CTRL BiTE group; $8 \times 10^6$ and $4 \times 10^6$ ROR1xCD3 BiTE groups 1 and 2 respectively). ROR1xCD3 and CD19xCD3 was injected daily at 10 μg/kg/mouse.

PANC-1.Luc engraftment was assessed by in vivo bioluminescent imaging (BLI) at day 3, 5 and 8 after injection. (b) Establish xenograft model: PANC-1 cell lines ($5 \times 10^6$) were injected in the right flank of immunocompromised athymic nude mice and xenografts were established to a minimum size of 100 mm$^3$. Mice received a single intravenous injection of purified T-cells ($5 \times 10^6$) and were treated with ROR1xCD3, CD19xCD3 or PBS at 10 μg/kg/day iv daily for 7 days and the size of the tumour measured by calliper.

(c) Established xenograft model: Follow-up of these animals showed that ROR1xCD3 treated mice had lower tumour volumes compared to the control cohorts on day 28.

Figure 3:
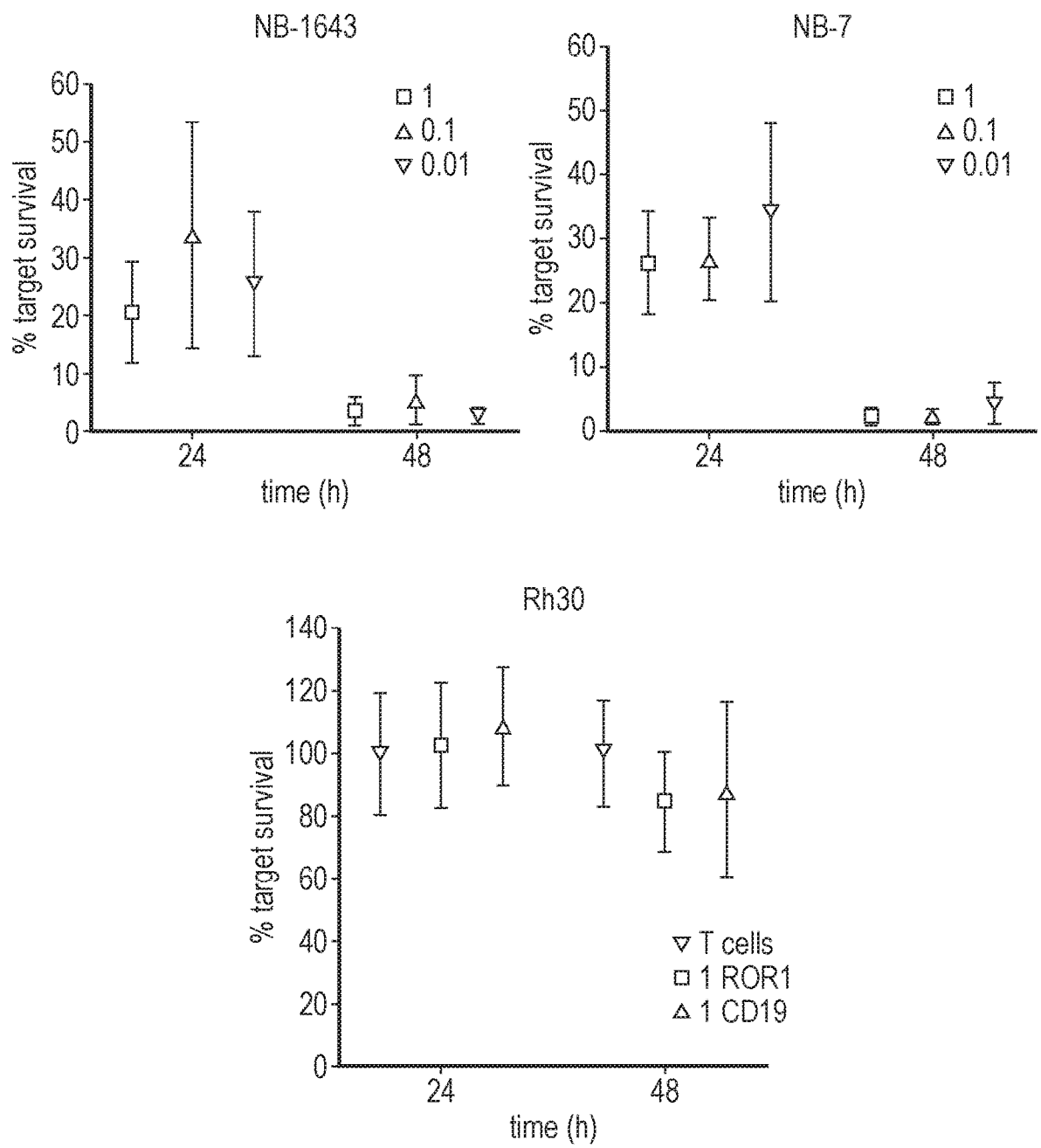

FIG. 3: Cytotoxicity against ROR1 positive neuroblastoma cell lines.

EXAMPLES

Materials and Methods

ScFv Generation

Rats were immunised against full length ROR1 by Aldevron GmBH and oligoclonal clones from the subsequent hybridomas were single cell sorted and variable sequences isolated by 5' Reverse Amplification of cDNA ends using standard laboratory protocols. Productive sequences were cloned into antibodies and assessed for specific ROR1 binding before being converted to single chain variable fragments in a heavy chain-linker-light chain format.

Cell Lines and Reagents

PANC-1, SKOV-3 and HEK293T cells were obtained from American Type Culture Collection (ATCC; Teddington, Middlesex, United Kingdom). SUIT-2, CFPAC1, HPAF-II MiaPaCa-2, PSN-1 cell lines were kindly provided by Professor Aldo Scarpa (Department of Pathology and Diagnostics, University and Hospital Trust of Verona, Verona, Italy). HEK293T cells were maintained in Iscove's Modified Dulbecco's Medium (ThermoScientific, Paisley, UK) supplemented with 10% fetal bovine serum (FBS) (ThermoScientific). All the other cell lines were maintained in RPMI-1640 medium (ThermoScientific) supplemented with 10% FBS. Cells were cultured at 37° C. with 5% CO2. Cell lines were assessed for ROR1 expression by staining with the anti-ROR1 clone 2A2 antibody (Biolegend, UK) by flow cytometry.

ROR1xCD3 Generation

The ROR1 and control CD19 fmc63 ScFvs were coupled to the anti-human CD3 ScFv (Clone OKT3) through a short amino acid linker using gBlocks (Integrated DNA Technologies, Leuven, Belgium) and overlapping extension PCR using Phusion DNA Polymerase (New England Biolabs, Ipswich, UK). The BiTE open reading frame (ORF) was cloned into the SFG retroviral vector upstream of a GFP ORF, by NcoI/MluI restriction digestion. The two ORFs are separated by an IRES region to obtain the SFG.ROR1xCD3.IRES.GFP or SFG.CD19xCD3.IRES.GFP. An N-terminal hexa-Histidine Tag was included to allow for detection and purification.

Generation of HEK293T stable BiTE producer cells.

Retroviral supernatant was produced in HEK293T cells using the RD114 retrovirus envelope (RDF), PeqPam3 gag-pol and SFG.ROR1xCD3.IRES.GFP or SFG.CD19xCD3.IRES.GFP vector following standard laboratory protocols.

Supernatants containing retrovirus were harvested 48 and 72 hours after transfection, immediately frozen on dry ice and stored at −80° C. until further use. HEK293T cells ($1.8 \times 10^6$) were plated in 10 cm dish in fresh media, and transduced with 2 ml of supernatant containing retrovirus at 24 and 48 hours post seeding. Transduced cells were then incubated for 72 hours in a humidified incubator at 37 C with 5% CO2, sorted based on GFP expression and tested for BiTE production.

ROR1xCD3 Production, Purification and Binding

HEK293T media containing ROR1xCD3 or CD19xCD3 was collected and purified by fast protein liquid chromatography (FPLC) using HiTrap Talon binding columns with an AKTA explorer (GE Healthcare Life Sciences, UK). Quality of the BiTEs was assessed by Coomassie staining after SDS-PAGE and quantified using BSA dilution standards (ThermoScientific). ImageJ software was used for data analysis (U. S. National Institutes of Health, Bethesda, Md., USA). ROR1xCD3 and CD19xCD3 were validated by western blot using an HRP conjugated anti-His antibody (Biolegend, UK). Specific binding of ROR1xCD3 or CD19xCD3 to target cells was assessed by flow cytometry using an anti His Tag antibody (Abcam, Cambridge, UK).

T Cells Purification

Peripheral blood mononuclear cells (PBMCs) from healthy donors were obtained after centrifugation of fresh blood on a density gradient using Ficoll-Paque Plus (GE Healthcare Life Sciences, UK). T-cells were purified using a human Pan T-Cell Isolation Kit (Miltenyi Biotec, Surrey, United Kingdom), and checked by flow cytometry for the quality of the isolation. In keeping with previous reports, freshly isolated T-cells were expanded for animal work only: T cells were plated at $1 \times 10^6$ cells per well in 24 wells plate and expanded using CD3/CD28 beads (ThermoScientific, UK), and kept in culture for 1 week before of being injected into the mice. Unstimulated T cells were used for all in vitro experiments.

Flow Cytometry

Data was captured on a LRS Fortessa II flow cytometer (Becton Dickinson, Oxford, UK) and analysed using FlowJo software (Flowjo LLC, Ashlard, Orgeon). Fluorescence activated cell sorting was undertaken on a FACSAria Cell Sorted (Becton Dickinson).

Co-Cultures Assay

Co-culture assays were performed in 96 well plates, containing $1 \times 10^4$ target cells, $1 \times 10^4$ T-cells and purified ROR1xCD3 BiTE (or CD19xCD3 as the control) at a concentration of 0.1 ng/ml to 1 µg/ml, as reported in the manuscript. Twenty-four hours after addition of ROR1xCD3 or CD19xCD3, supernatant was collected for cytokine evaluation, which was performed by ELISA following the manufacturer's instructions (Biolegend, UK). To assess cytotoxicity we used The CellTiter 96® AQueous One Solution Cell Proliferation Assay (MTS) following the manufacturer protocol (Promega, UK).

Statistics

Statistical analysis was undertaken in GraphPad Prism Version 6 for Windows (GraphPad Software, La Jolla Calif. USA). Statistical significance was taken when p<0.05 and error bars represent standard error of the mean.

Animal Studies

All animal work was performed under the authority of the United Kingdom Home Office Project and Personal License regulations and was compliant with the guidelines of the University College London. Mice were obtained from Charles River Laboratories Inc. Six- to eight-week-old female Hsd:Athymic Nude-Foxn1$^{nu}$ mice received $2 \times 10^6$ PANC-1.Luc cells by intraperitoneal injection. At 3, 5 and 8 days or 14 days later PANC-1.Luc luciferase expression was detected using D-Luciferin (Melford Laboratories), which was injected intraperitoneally (IP) at a dose of 200 µg/mouse, and imaged using the IVIS Imaging System 100 Series (Perkin Elmer). Living Image 4.4 software was used to quantify bioluminescence imaging (BLI) signals, and ROI detection was created for quantification compared for BLI intensity. For xenograft studies $5 \times 10^6$ of PANC-1 cells were injected in the flank of 6-8-week-old Hsd:Athymic Nude-Foxn1$^{nu}$ mice. Once the xenograft were established (minimum size 100 mm$^3$) mice received $5 \times 10^6$ T-cells by single tail vein injection, followed by a daily injection of PBS or ROR1xCD3/CD19xCD3 suspended in 0.1% BSA in PBS (10 rig/kg/mouse). Tumour volume was calculated using the ellipsoidal formula (length×width$^2$)/2.

Results and Discussion

From a panel of anti-ROR1 antibodies isolated from a rat hybridoma library we determined two lead candidates that bound either the membrane distal Immunoglobulin like domain or the more proximal Frizzled domain of ROR1. These were converted into a single chain variable fragments (scFv) format prior to coupling with a CD3 scFv in a tandem structure separated by a short linker. Within this ROR1-BiTE, we included an N-terminal hexa-Histidine tag to allow for detection and purification, which did not compromise the ability to independently bind CD3 or ROR1 with each arm. Direct comparison of the two ROR1-BiTEs showed superior cytotoxicity with the membrane proximal binding BiTE specific for the Frizzled domain, which was selected for further evaluation (ROR1xCD3).

The inventors focused on pancreatic cancer and co-culture of ROR1 positive PANC-1 cells, a pancreatic ductal adenocarcinoma cell line, with unstimulated T cells at a 1:1 effector:target ratio (E:T) in the presence of ROR1xCD3 demonstrated significant cytotoxicity as assessed by a cellular viability assay at 24 hours compared with a control CD19 BiTE (CD19xCD3) (p<0.001) (FIG. 1a). Cytotoxicity was associated with 15 fold increase in interferon-γ (IFNγ) and 11 fold increase in interleukin-2 (IL-2) compared to co-cultures with CD19xCD3 (FIG. 1b). Importantly, cytotoxicity was not observed in co-cultures with T-cells alone or with ROR1xCD3 alone, confirming both ROR1xCD3 and T-cells are required for effector function. Dose dependent cytotoxicity with ROR1xCD3 was observed across a wide panel of positive pancreatic cell lines comprising, PANC-1, SUIT-2, CFPAC1, HPAF-II, MiaPaCa2 and PSN-1, with significant activity even at concentrations of 0.1 ng/ml (FIG. 1c).

Models of pancreatic cancer are limited in their reproduction of the complex tumour environment, however, to provide proof of concept and in keeping with other studies, ROR1 BiTE was assessed in two xenograft models. First, $2 \times 10^6$ PANC-1, firefly luciferase-positive cells (PANC-1.Luc) were injected into the peritoneal-cavity of athymic nude mice followed by a single bolus administration of either $4 \times 10^6$ (E:T ratio of 2:1) or $8 \times 10^6$ (E:T ratio of 4:1) human T-cells. Mice received a daily intraperitoneal injection of ROR1xCD3 or control CD19xCD3 at a dose of 10 rig/kg/mouse. Analysis on day 8 revealed PANC-1.Luc engraftment, as assessed by non-invasive bioluminescence imaging (BLI), was reduced in a T-cell dose dependent manner by 11- or 15-fold in the 2:1 and 4:1 cohorts of mice respectively, compared to animals that received CD19xCD3 (FIG. 2a).

Then a more challenging subcutaneous model was undertaken in which $5 \times 10^6$ PANC-1 cells were injected into the right flank of athymic nude mice and allowed to establish to a minimum size of 100 mm$^3$. Animals subsequently received a single tail vein administration of $5 \times 10^6$ purified T-cells followed by intraperitoneal administration of ROR1xCD3 at a dose of 10 µg/kg/mouse daily for 7 days without exogenous cytokine support. Control cohorts received either CD19xCD3 at an identical dosing regimen or excipient (PBS). Treatment with ROR1xCD3 reduced the growth of xenografts by >50% during the treatment period at 7 days compared to control animals (mean size 62.2 mm$^3$ vs 119.7 mm$^3$, p=0.003) (FIG. 2b). Moreover, longer follow-up of these animals showed that despite only 7 days of therapy, ROR1xCD3 treated mice had lower tumour volumes compared to the control cohorts on day 28 (mean size 171.2 mm$^3$ vs 361.2 mm³, p=0.037), suggesting transient treatment with ROR1xCD3 can lead to a durable anti-tumour response. This was in the context of a single low dose T-cell infusion and with a relatively low dose of BiTE (FIG. 2c).

No toxicity was observed in terms of behaviour, physical appearance or distress in either of these mouse models despite the fact that the ROR1 ScFv binds to both human and murine ROR1.

Given ROR1 is expressed on a range of solid malignancies, irrespective of cell of origin, we investigated the wider applicability of using ROR1xCD3 against cell lines representative of melanoma (T618A), glioblastoma (U-251, A 172), ovarian (SKOV-3, HOC-7, HEY), prostate (DU145, PC-3), breast (MDA-MB-231) and hepatic cancers (HUH7, SK-Hep-1), all of which are ROR1 positive. ROR1xCD3 was able to drive significant T cell mediated cytotoxicity against all of these cell lines compared to treatment with CD19xCD3. Specificity was further demonstrated as no cytotoxicity was observed against the ROR1 negative breast cancer MCF-7 cell line.

In conclusion, there is described the development and characterisation of a novel BiTE that elicits tumour cytotoxicity following simultaneously binding to both the T cell and ROR1 positive tumour cells. This circumvents the potential for undesired T-cell activation and makes BiTE molecules exquisitely selective for ROR1, a target that is expressed at high levels on an array of tumours including pancreatic cancer. Efficacy was further established in two xenograft models of pancreatic cancer with significant and durable decreases in tumour burden despite animals only receiving a single low dose infusion of T-cells and relatively low doses of BiTE.

To our knowledge, this is the first direct evidence of efficacy with a BiTE that targets ROR1, a molecule that is expressed at high levels on aggressive tumours and is associated with epithelial-mesenchymal transition and metastasis. A real appeal of ROR1-BiTEs is their potential to target cancer stem cells, which express ROR1 in the ovarian cancer and glioblastoma setting and raises the potential for targeting of chemo/radiotherapy resistant cancer initiating stem cells.

ROR1 specific Chimeric Antigen Receptor (CAR) T-cells are being tested against haematological and solid malignancies (NCT02194374, NCT02706392), however BiTEs offer advantages as they are easier to manufacture at scale, simpler to administer and avoid the need for expensive and time consuming manipulation of patient-specific T-cell including ex vivo expansion and transduction. Furthermore, BiTEs are rapidly cleared from the body, minimising the risk of unexpected untoward toxicity.

Example 2

Epitope Mapping

To assess the epitope of the generated antibodies we produced cell lines with truncated ROR1: these comprised SUPT1 cells expressing full length ROR1 (Immunoglobulin domain, Frizzled domain and Kringle Domain), Immunoglobulin only SupT1, Frizzled Only SupT1, Kringle Only SupT1 and combinations (Ig and Frizzled SupT1 and Frizzled and Kringle SupT1). This demonstrated that Clone F bound to the Frizzled domain. This is different to the prior art antibodies R12 and 4A5 which bind the immunoglobulin domain. Therefore, clone F shows different and distinct binding characteristics compared to prior art antibodies R12 and 4A5.

To further characterize the epitope that Clone F bound specifically we compared rat ROR1 to human ROR1 to assess differences in amino acid between these two species. We made a number of mutated human ROR1 constructs that included single amino acid substitutions to putative amino acids that these antibodies could bind to further characterize the epitope in question.

For clone F, point mutations were generated for the Fz domain of human ROR1 at positions 254 and 261. The particular mutations used were I(254)V and Q(261)H.

It was found that the Q(261)H substitution reduced or stopped the clone F antibody binding to ROR1-Fz domain, whereas the I(254)V substitution did not seem to affect binding. Further, the combination of Q(261)H and I(254)V also prevented antibody binding. Therefore, Gln-261 is essential for antibody binding.

Example 3

Clone F is Unique to Other Antibodies Generated (Murine and Rabbit) Because of Sequence Homology Human, murine, rabbit and rat ROR1 protein sequences were aligned using Uniprot web based software (http://www.uniprot.org/align/) and the variation between the different species highlighted. Uniprot accession numbers: Human (Q01973), Murine (Q9Z139) and Rabbit (G1U5L1). For rat ROR1, NCBI reference sequence NP_001102141.1 was used as the corresponding Uniprot sequence was only partially complete.

Clone F binds to Q261, which was possible due to differences between rat and human amino acids at this position (the human amino acid at position 261 is glutamine (Q) whereas the corresponding amino acid at this position in rat is histidine (H)). When rats are immunised with human ROR1, this amino acid difference is recognised as an immunogen relative to the rat ROR1 sequence, against which an antibody is produced.

The known antibody R12 (rabbit) and murine ROR1 binders show homology with human ROR1 at this site (i.e. they all have glutamine (Q) at this position). As a result, immunisation of rabbits or mice with human ROR1 does not result in antibody production directed to this position as it is not immunogenic. In view of this, clone F is unique in its ability to bind to this epitope.

Example 4

Clone F BiTE Leads to Significant Cytotoxicity of ROR1 Positive Neuroblastoma Cell Lines Clone F ROR1 BITE leads to significant cytotoxicity of ROR1 positive NB-1643 and NB-7 neuroblastoma cell lines but not Rh30 ROR1 negative cell lines, even at concentrations of 0.01 micrograms/ml (see FIG. 3).

Example 5

Humanisation of Clone F Imparts Advantages Compared to Non-Humanised Comparator Constructs One of the rationales for targeting ROR1 as opposed to CD19, is sparing of the normal ROR1 negative B cell population. However at the same time, continued presence of normal CD19+ B cells allows for immune responses directed against a rat derived scFv. This has been seen with murine scFvs and have led to clinically significant outcomes, including anaphylaxis with mRNA modified mesothelin CAR T cells (Maus et al., 2013) or antibody responses, with α-folate receptor or carbonic anhydrase IX specific CAR T cells (Lamers et al., 2006, Kershaw et al., 2006). T cell mediated immune responses are also possible due to cross presentation of components of the CAR on MHC. CD19 CAR T cells by comparison, inherently neutralise the risk of antibody based immune responses by eradicating the normal B cell population, with B cell recurrence associated with a higher risk of relapse.

By undertaking humanisation of Clone F we have decreased the likelihood of immune responses against the BiTE leading to enhanced persistence and decreased immunogenicity.

SEQUENCE LISTING

The amino acid sequences listed below are shown using standard one letter codes for amino acids. The sequences are for clone F and the five humanised variable sequences that were developed.

The variable regions of the heavy and light chains of Clone F described above and the humanised versions of this clone are as follows:

```
Clone F light chain variable region
                                        (SEQ ID NO. 3)
DIQMTQSPSFLSASVGDRVTINCKASQNIDRYLNWYQQKLGEAPKRLLY

NTNKLQTGIPSRFSGSGSATDFTLTISSLQPEDFATYFCLQYNSLPLTF

GSGTKLEIK

Humanised 1 light chain variable region
                                        (SEQ ID NO. 4)
DIQMTQSPSSLSASVGDRVTITCKASQNIDRYLNWYQQKPGKAPKRLIY

NTNKLQTGVPSRFSGSGSGTEFTLTISSLQPEDFATYYCLQYNSLPLTF

GQGTKLEIK

Humanised 2 light chain variable region
                                        (SEQ ID NO. 5)
DIQMTQSPSSLSASVGDRVTITCKASQNIDRYLNWFQQKPGKAPKSLIY

NTNKLQTGVPSKFSGSGSGTDFTLTISSLQPEDFATYYCLQYNSLPLTF

GQGTRLEIK

Humanised 3 light chain variable region
                                        (SEQ ID NO. 6)
DIQMTQSPSSLSASVGDRVTITCKASQNIDRYLNWYQQKPGKAPKLLIY

NTNKLQTGVPSRFSGSGSGTDFTLTISSLQPEDFATYYCLQYNSLPLTF

GQGTKLEIK

Humanised 4 light chain variable region
                                        (SEQ ID NO. 7)
DIQLTQSPSFLSASVGDRVTITCKASQNIDRYLNWYQQKPGKAPKLLIY

NTNKLQTGVPSRFSGSGSGTEFTLTISSLQPEDFATYYCLQYNSLPLTF

GQGTKLEIK

Humanised 5 light chain variable region
                                        (SEQ ID NO. 8)
DIQMTQSPSTLSASVGDRVTITCKASQNIDRYLNWYQQKPGKAPKLLIY

NTNKLQTGVPSRFSGSGSGTEFTLTISSLQPDDFATYYCLQYNSLPLTF

GQGTKLEIK

Clone F heavy chain variable region
                                        (SEQ ID NO. 9)
EVQLVESGGGLVQPGRSLKLSCAASGFIFSEHNMAWVRQAPKKGLEWVA

TISDDGRNTYYRDSMRGRFTISRENARSTLYLQLDSLRSEDTATYYCAS

HRYNLFDSWGQGVMVTVSS

Humanised 1 heavy chain variable region
                                        (SEQ ID NO. 10)
QVQLVESGGGVVQPGRSLRLSCAASGFIFSEHNMAWVRQAPGKGLEWVA

TISDDGRNTYYRDSMRGRFTISRDNSKNTLYLQMNSLRAEDTAVYYCTS

HRYNLFDSWGQGTMVTVSS

Humanised 2 heavy chain variable region
                                        (SEQ ID NO. 11)
EVQLVESGGGLVQPGGSLRLSCAASGFIFSEHNMAWVRQAPGKGLEWVS

TISDDGRNTYYRDSMRGRFTISRDNSKNTLYLQMNSLRAEDTAVYYCAK

HRYNLFDSWGQGTLVTVSS

Humanised 3 heavy chain variable region
                                        (SEQ ID NO. 12)
EVQLVESGGGLVQPGGSLRLSCAASGFIFSEHNMAWVRQAPGKGLEWVA

TISDDGRNTYYRDSMRGRFTISRDNAKNSLYLQMNSLRAEDTAVYYCAR

HRYNLFDSWGQGTMVTVSS

Humanised 4 heavy chain variable region
                                        (SEQ ID NO. 13)
EVQLVESGGGLVQPGGSLRLSCAASGFIFSEHNMAWVRQAPGKGLVWVS

TISDDGRNTYYRDSMRGRFTISRDNAKNTLYLQMNSLRAEDTAVYYCAR

HRYNLFDSWGQGTLVTVSS

Humanised 5 heavy chain variable region
                                        (SEQ ID NO. 14)
EVQLVESGGGLVQPGRSLRLSCAASGFIFSEHNMAWVRQAPGKGLEWVS

TISDDGRNTYYRDSMRGRFTISRDNAKNSLYLQMNSLRAEDTALYYCAK

HRYNLFDSWGQGTLVTVSS
```

The three CDR sequences in each of the variable regions above are underlined. These CDR sequences have been determined based on information on framework regions and CDRs from the IMGT (the international ImMunoGeneTics information system) database (see www.imgt.org).

Further sequences related to those above and their relevant sequence identifier numbers (SED ID NOs) are given below:

| Sequence | Description | SEQ ID NO: |
|---|---|---|
| DIQMTQSPSFLSASVGDRVTINCKAS | Rat Light Chain Framework Region 1 | 15 |
| QNIDRY | Rat Light Chain CDR1 | 16 |
| LNWYQQKLGEAPKRLLY | Rat Light Chain Framework Region 2 | 17 |
| NTN | Rat Light Chain CDR2 | 18 |
| KLQTGIPSRFSGSGSATDFTLTISSL QPEDFATYFC | Rat Light Chain Framework Region 3 | 19 |

-continued

| Sequence | Description | SEQ ID NO: |
|---|---|---|
| LQYNSLPLT | Rat Light Chain CDR3 | 20 |
| FGSGTKLEIK | Rat Light Chain Framework Region 4 | 21 |
| EVQLVESGGGLVQPGRSLKLSCAAS | Rat Heavy Chain Framework Region 1 | 22 |
| GFIFSEHN | Rat Heavy Chain CDR1 | 23 |
| MAWVRQAPKKGLEWVAT | Rat Heavy Chain Framework Region 2 | 24 |
| ISDDGRNT | Rat Heavy Chain CDR2 | 25 |
| YYRDSMRGRFTISRENARSTLYLQLDSLRSEDTATYYC | Rat Heavy Chain Framework Region 3 | 26 |
| ASHRYNLFDS | Rat Heavy Chain CDR3 | 27 |
| WGQGVMVTVSS | Rat Heavy Chain Framework Region 4 | 28 |
| DIQMTQSPSSLSASVGDRVTITCKAS | Humanised 1 Light Chain FW Region 1 | 29 |
| QNIDRY | Humanised 1 Light Chain CDR1 | 16 |
| LNWYQQKPGKAPKRLIY | Humanised 1 Light Chain FW Region 2 | 30 |
| NTN | Humanised 1 Light Chain CDR2 | 18 |
| KLQTGVPSRFSGSGSGTEFTLTISSLQPEDFATYYC | Humanised 1 Light Chain FW Region 3 | 31 |
| LQYNSLPLT | Humanised 1 Light Chain CDR3 | 20 |
| FGQGTKLEIK | Humanised 1 Light Chain FW Region 4 | 32 |
| QVQLVESGGGVVQPGRSLRLSCAAS | Humanised 1 Heavy Chain FW Region 1 | 33 |
| GFIFSEHN | Humanised 1 Heavy Chain CDR1 | 23 |
| MAWVRQAPGKGLEWVAT | Humanised 1 Heavy Chain FW Region 2 | 34 |
| ISDDGRNT | Humanised 1 Heavy Chain CDR2 | 25 |
| YYRDSMRGRFTISRDNSKNTLYLQMNSLRAEDTAVYYCTS | Humanised 1 Heavy Chain FW Region 3 | 35 |
| TSHRYNLFDS | Humanised 1 Heavy Chain CDR3 | 36 |
| WGQGTMVTVSS | Humanised 1 Heavy Chain FW Region 4 | 37 |
| DIQMTQSPSSLSASVGDRVTITCKAS | Humanised 2 Light Chain FW Region 1 | 29 |
| QNIDRY | Humanised 2 Light Chain CDR1 | 16 |
| LNWFQQKPGKAPKSLIY | Humanised 2 Light Chain FW Region 2 | 38 |
| NTN | Humanised 2 Light Chain CDR2 | 18 |
| KLQTGVPSKFSGSGSGTDFTLTISSLQPEDFATYYC | Humanised 2 Light Chain FW Region 3 | 39 |
| LQYNSLPLT | Humanised 2 Light Chain CDR3 | 20 |
| FGQGTRLEIK | Humanised 2 Light Chain FW Region 4 | 40 |
| EVQLVESGGGLVQPGGSLRLSCAAS | Humanised 2 Heavy Chain FW Region 1 | 41 |
| GFIFSEHN | Humanised 2 Heavy Chain CDR1 | 23 |
| MAWVRQAPGKGLEWVST | Humanised 2 Heavy Chain FW Region 2 | 42 |
| ISDDGRNT | Humanised 2 Heavy Chain CDR2 | 25 |
| YYRDSMRGRFTISRDNSKNTLYLQMNSLRAEDTAVYYCAK | Humanised 2 Heavy Chain FW Region 3 | 43 |
| AKHRYNLFDS | Humanised 2 Heavy Chain CDR3 | 44 |
| WGQGTLVTVSS | Humanised 2 Heavy Chain FW Region 4 | 45 |
| DIQMTQSPSSLSASVGDRVTITCKAS | Humanised 3 Light Chain FW Region 1 | 29 |
| QNIDRY | Humanised 3 Light Chain CDR1 | 16 |
| LNWYQQKPGKAPKLLIY | Humanised 3 Light Chain FW Region 2 | 46 |
| NTN | Humanised 3 Light Chain CDR2 | 18 |
| KLQTGVPSRFSGSGSGTDFTLTISSLQPEDFATYYC | Humanised 3 Light Chain FW Region 3 | 47 |
| LQYNSLPLT | Humanised 3 Light Chain CDR3 | 20 |
| FGQGTKLEIK | Humanised 3 Light Chain FW Region 4 | 32 |
| EVQLVESGGGLVQPGGSLRLSCAAS | Humanised 3 Heavy Chain FW Region 1 | 41 |
| GFIFSEHN | Humanised 3 Heavy Chain CDR1 | 23 |
| MAWVRQAPGKGLEWVAT | Humanised 3 Heavy Chain FW Region 2 | 34 |
| ISDDGRNT | Humanised 3 Heavy Chain CDR2 | 25 |
| YYRDSMRGRFTISRDNAKNSLYLQMNSLRAEDTAVYYCAR | Humanised 3 Heavy Chain FW Region 3 | 48 |
| ARHRYNLFDS | Humanised 3 Heavy Chain CDR3 | 49 |

| Sequence | Description | SEQ ID NO: |
|---|---|---|
| WGQGTMVTVSS | Humanised 3 Heavy Chain FW Region 4 | 37 |
| DIQLTQSPSFLSASVGDRVTITCKAS | Humanised 4 Light Chain FW Region 1 | 50 |
| QNIDRY | Humanised 4 Light Chain CDR1 | 16 |
| LNWYQQKPGKAPKLLIY | Humanised 4 Light Chain FW Region 2 | 46 |
| NTN | Humanised 4 Light Chain CDR2 | 18 |
| KLQTGVPSRFSGSGSGTEFTLTISSLQPEDFATYYC | Humanised 4 Light Chain FW Region 3 | 31 |
| LQYNSLPLT | Humanised 4 Light Chain CDR3 | 20 |
| FGQGTKLEIK | Humanised 4 Light Chain FW Region 4 | 32 |
| EVQLVESGGGLVQPGGSLRLSCAAS | Humanised 4 Heavy Chain FW Region 1 | 41 |
| GFIFSEHN | Humanised 4 Heavy Chain CDR1 | 23 |
| MAWVRQAPGKGLVWVST | Humanised 4 Heavy Chain FW Region 2 | 51 |
| ISDDGRNT | Humanised 4 Heavy Chain CDR2 | 25 |
| YYRDSMRGRFTISRDNAKNTLYLQMNSLRAEDTAVYYCAR | Humanised 4 Heavy Chain FW Region 3 | 52 |
| ARHRYNLFDS | Humanised 4 Heavy Chain CDR3 | 49 |
| WGQGTLVTVSS | Humanised 4 Heavy Chain FW Region 4 | 45 |
| DIQMTQSPSTLSASVGDRVTITCKAS | Humanised 5 Light Chain FW Region 1 | 53 |
| QNIDRY | Humanised 5 Light Chain CDR1 | 16 |
| LNWYQQKPGKAPKLLIY | Humanised 5 Light Chain FW Region 2 | 46 |
| NTN | Humanised 5 Light Chain CDR2 | 18 |
| KLQTGVPSRFSGSGSGTEFTLTISSLQPDDFATYYC | Humanised 5 Light Chain FW Region 3 | 54 |
| LQYNSLPLT | Humanised 5 Light Chain CDR3 | 20 |
| FGQGTKLEIK | Humanised 5 Light Chain FW Region 4 | 32 |
| EVQLVESGGGLVQPGRSLRLSCAAS | Humanised 5 Heavy Chain FW Region 1 | 55 |
| GFIFSEHN | Humanised 5 Heavy Chain CDR1 | 23 |
| MAWVRQAPGKGLEWVST | Humanised 5 Heavy Chain FW Region 2 | 42 |
| ISDDGRNT | Humanised 5 Heavy Chain CDR2 | 25 |
| YYRDSMRGRFTISRDNAKNSLYLQMNSLRAEDTALYYCAK | Humanised 5 Heavy Chain FW Region 3 | 56 |
| AKHRYNLFDS | Humanised 5 Heavy Chain CDR3 | 44 |
| WGQGTLVTVSS | Humanised 5 Heavy Chain FW Region 4 | 45 |
| XXHRYNLFDS (where $X_1$ is A or T and $X_2$ is S, K or R) | General Heavy Chain CDR3 | 57 |

An alternative method for labelling CDRs is using the Kabat system and this can give slightly different results. However, this can easily be determined by someone skilled in the art. For the avoidance of doubt, the CDR sequences in the variable regions based on the Kabat system are as follows, where the Kabat CDRs are in bold:

```
Clone F light chain variable region
                                       (SEQ ID NO. 3)
DIQMTQSPSFLSASVGDRVTINCKASQNIDRYLNWYQQKLGEAPKRLLY

NTNKLQTGIPSRFSGSGSATDFTLTISSLQPEDFATYFCLQYNSLPLTF

GSGTKLEIK

Humanised 1 light chain variable region
                                       (SEQ ID NO. 4)
DIQMTQSPSSLSASVGDRVTITCKASQNIDRYLNWYQQKPGKAPKRLIY

NTNKLQTGVPSRFSGSGSGTEFTLTISSLQPEDFATYYCLQYNSLPLTF

GQGTKLEIK

Humanised 2 light chain variable region
                                       (SEQ ID NO. 5)
DIQMTQSPSSLSASVGDRVTITCKASQNIDRYLNWFQQKPGKAPKSLIY

NTNKLQTGVPSKFSGSGSGTDFTLTISSLQPEDFATYYCLQYNSLPLTF

GQGTRLEIK

Humanised 3 light chain variable region
                                       (SEQ ID NO. 6)
DIQMTQSPSSLSASVGDRVTITCKASQNIDRYLNWYQQKPGKAPKLLIY

NTNLQTGVPSRFSGSGSGTDFTLTISSLQPEDFATYYCLQYNSLPLTFG

QGTKLEIK

Humanised 4 light chain variable region
                                       (SEQ ID NO. 7)
DIQLTQSPSFLSASVGDRVTITCKASQNIDRYLNWYQQKPGKAPKLLIY

NTNKLQTGVPSRFSGSGSGTEFTLTISSLQPEDFATYYCLQYNSLPLTF

GQGTKLEIK

Humanised 5 light chain variable region
                                       (SEQ ID NO. 8)
DIQMTQSPSTLSASVGDRVTITCKASQNIDRYLNWYQQKPGKAPKLLIY

NTNKLQTGVPSRFSGSGSGTEFTLTISSLQPDDFATYYCLQYNSLPLTF

GQGTKLEIK
```

```
Clone F heavy chain variable region
                                         (SEQ ID NO. 9)
EVQLVESGGGLVQPGRSLKLSCAASGFIFSEHNMAWVRQAPKKGLEWVA

TISDDGRNTYYRDSMRGRFTISRENARSTLYLQLDSLRSEDTATYYCAS

HRYNLFDSWGQGVMVTVSS

Humanised 1 heavy chain variable region
                                         (SEQ ID NO. 10)
QVQLVESGGGVVQPGRSLRLSCAASGFIFSEHNMAWVRQAPGKGLEWVA

TISDDGRNTYYRDSMRGRFTISRDNSKNTLYLQMNSLRAEDTAVYYCTS

HRYNLFDSWGQGTMVTVSS

Humanised 2 heavy chain variable region
                                         (SEQ ID NO. 11)
EVQLVESGGGLVQPGGSLRLSCAASGFIFSEHNMAWVRQAPGKGLEWVS

TISDDGRNTYYRDSMRGRFTISRDNSKNTLYLQMNSLRAEDTAVYYCAK

HRYNLFDSWGQGTLVTVSS

Humanised 3 heavy chain variable region
                                         (SEQ ID NO. 12)
EVQLVESGGGLVQPGGSLRLSCAASGFIFSEHNMAWVRQAPGKGLEWVA

TISDDGRNTYYRDSMRGRFTISRDNAKNSLYLQMNSLRAEDTAVYYCAR

HRYNLFDSWGQGTMVTVSS

Humanised 4 heavy chain variable region
                                         (SEQ ID NO. 13)
EVQLVESGGGLVQPGGSLRLSCAASGFIFSEHNMAWVRQAPGKGLVWVS

TISDDGRNTYYRDSMRGRFTISRDNAKNTLYLQMNSLRAEDTAVYYCAR

HRYNLFDSWGQGTLVTVSS

Humanised 5 heavy chain variable region
                                         (SEQ ID NO. 14)
EVQLVESGGGLVQPGRSLRLSCAASGFIFSEHNMAWVRQAPGKGLEWVS

TISDDGRNTYYRDSMRGRFTISRDNAKNSLYLQMNSLRAEDTALYYCAK

HRYNLFDSWGQGTLVTVSS
```

Therefore, the CDRs when determined using the Kabat system are as follows:

| Sequence | Description | SEQ ID NO: |
|---|---|---|
| KASQNIDRYLN | Light Chain CDR1 | 58 |
| NTNKLQT | Light Chain CDR2 | 59 |
| LQYNSLPLT | Light Chain CDR3 | 20 |
| EHNMA | Heavy Chain CDR1 | 60 |
| TISDDGRNTYYRDSMRG | Heavy Chain CDR2 | 61 |
| HRYNLFDS | Heavy Chain CDR3 | 62 |

Exemplary sequences for variable regions for binding CD3 are as follows with the CDRs underlined:

```
Mouse light chain variable region
                                         (SEQ ID NO. 63)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEIN

Humanised 1 light chain variable region
                                         (SEQ ID NO. 64)
EIVLTQSPATLSLSPGERATLSCSASSSVSYMNWYQQKPGQAPRLLIYD

TSKLASGIPARFSGSGSGTDFTLTISSLEPEDFAVYYCQQWSSNPFTFG

QGTKLEIK

Humanised 2 light chain variable region
                                         (SEQ ID NO. 65)
DIQMTQSPSSLSASVGDRVTITCSASSSVSYMNWYQQKPGKAPKLLIYD

TSKLASGVPSRFSGSGSGTDFTLTISSLQPEDFATYYCQQWSSNPFTFG

QGTKLEIK

Humanised 3 light chain variable region
                                         (SEQ ID NO. 66)
DIQLTQSPSFLSASVGDRVTITCSASSSVSYMNWYQQKPGKAPKLLIYD

TSKLASGVPSRFSGSGSGTEFTLTISSLQPEDFATYYCQQWSSNPFTFG

QGTKLEIK

Humanised 4 light chain variable region
                                         (SEQ ID NO. 67)
DIQMTQSPSTLSASVGDRVTITCSASSSVSYMNWYQQKPGKAPKLLIYD

TSKLASGVPSRFSGSGSGTEFTLTISSLQPDDFATYYCQQWSSNPFTFG

QGTKLEIK

Humanised 5 light chain variable region
                                         (SEQ ID NO. 68)
DIQMTQSPSSLSASVGDRVTITCSASSSVSYMNWYQQKPGKAPKRLIYD

TSKLASGVPSRFSGSGSGTEFTLTISSLQPEDFATYYCQQWSSNPFTFG

QGTKVEIK

Mouse heavy chain variable region
                                         (SEQ ID NO. 69)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YDDHYCLDYWGQGTTLTVSS

Humanised 1 heavy chain variable region
                                         (SEQ ID NO. 70)
QVQLVQSGAEVKKPGASVKVSCKASGYTFTRYTMHWVRQAPGQGLEWMG

YINPSRGYTNYNQKFKDRVTMTRDTSTSTVYMELSSLRSEDTAVYYCAR

YDDHYCLDYWGQGTLVTVSS

Humanised 2 heavy chain variable region
                                         (SEQ ID NO. 71)
QVQLVQSGAEVKKPGASVKVSCKASGYTFTRYTMHWVRQAPGQRLEWMG

YINPSRGYTNYNQKFKDRVTITRDTSASTAYMELSSLRSEDTAVYYCAR

YDDHYCLDYWGQGTLVTVSS
```

Humanised 3 heavy chain variable region
(SEQ ID NO. 72)
QVQLVQSGAEVKKPGSSVKVSCKASGYTFTRYTMHWVRQAPGQGLEWMG
YINPSRGYTNYNQKFKDRVTITADKSTSTAYMELSSLRSEDTAVYYCAR
YYDDHYCLDYWGQGTMVTVSS Humanised 4 heavy chain variable region
(SEQ ID NO. 73)
QVQLVESGGGLVKPGGSLRLSCAASGYTFTRYTMHWIRQAPGKGLEWVS
YINPSRGYTNYNQKFKDRFTISRDNAKNSLYLQMNSLRAEDTAVYYCAR
YYDDHYCLDYWGQGTTVTVSS Humanised 5 heavy chain variable region
(SEQ ID NO. 74)
EVQLVESGGGLVQPGGSLRLSCAASGYTFTRYTMHWVRQAPGKGLEWVS
YINPSRGYTNYNQKFKDRFTISRDNSKNTLYLQMNSLRAEDTAVYYCAK
YYDDHYCLDYWGQGTLVTVSS ROR1xCD3 bispecific antibody amino acid sequence
(SEQ ID NO. 75)
QVQLVESGGGVVQPGRSLRLSCAASGFIFSEHNMAWVRQAPGKGLEWVA
TISDDGRNTYYRDSMRGRFTISRDNSKNTLYLQMNSLRAEDTAVYYCTS
HRYNLFDSWGQGTMVTVSSGGGGSGGGGSGGGGSDIQMTQSPSSLSASV
GDRVTITCKASQNIDRYLNWYQQKPGKAPKRLIYNTNKLQTGVPSRFSG
SGSGTEFTLTISSLQPEDFATYYCLQYNSLPLTFGQGTKLEIKSGSGGG
GSQVQLVQSGAEVKKPGSSVKVSCKASGYTFTRYTMHWVRQAPGQGLEW
MGYINPSRGYTNYNQKFKDRVTITADKSTSTAYMELSSLRSEDTAVYYC
ARYYDDHYCLDYWGQGTMVTVSSVEGGSGGSGGSGGSGGVDDIQMTQSP
SSLSASVGDRVTITCSASSSVSYMNWYQQKPGKAPKRLIYDTSKLASGV
PSRFSGSGSGTEFTLTISSLQPEDFATYYCQQWSSNPFTFGQGTKVEIK ROR1xCD3 bispecific antibody amino acid sequence
with an N-terminal hexa-histidine tag
(SEQ ID NO. 76)
QVQLVESGGGVVQPGRSLRLSCAASGFIFSEHNMAWVRQAPGKGLEWVA
TISDDGRNTYYRDSMRGRFTISRDNSKNTLYLQMNSLRAEDTAVYYCTS
HRYNLFDSWGQGTMVTVSSGGGGSGGGGSGGGGSDIQMTQSPSSLSASV
GDRVTITCKASQNIDRYLNWYQQKPGKAPKRLIYNTNKLQTGVPSRFSG
SGSGTEFTLTISSLQPEDFATYYCLQYNSLPLTFGQGTKLEIKSGSGGG
GSQVQLVQSGAEVKKPGSSVKVSCKASGYTFTRYTMHWVRQAPGQGLEW
MGYINPSRGYTNYNQKFKDRVTITADKSTSTAYMELSSLRSEDTAVYYC
ARYYDDHYCLDYWGQGTMVTVSSVEGGSGGSGGSGGSGGVDDIQMTQSP
SSLSASVGDRVTITCSASSSVSYMNWYQQKPGKAPKRLIYDTSKLASGV
PSRFSGSGSGTEFTLTISSLQPEDFATYYCQQWSSNPFTFGQGTKVEIK
HHHHHH

---

The invention claimed is:

1. A bispecific antibody comprising a first antigen binding domain which selectively binds to Receptor Tyrosine Kinase Like Orphan Receptor 1 (ROR1); and a second antigen binding domain which selectively binds to the CD3 subunit of the T-Cell Receptor (TCR);

wherein the first antigen binding domain comprises a light chain variable domain and a heavy chain variable domain, wherein the light chain variable domain comprises a light chain complementarity determining region (LCDR)1, an LCDR2 and an LCDR3, wherein LCDR1 comprises the amino acid sequence set forth in SEQ ID NO: 16; LCDR2 comprises the amino acid sequence set forth in SEQ ID NO: 18; and LCDR3 comprises the amino acid sequence set forth in SEQ ID NO: 20; and wherein the heavy chain variable domain comprises a heavy chain complementarity determining region (HCDR)1, an HCDR2 and an HCDR3, wherein HCDR1 comprises the amino acid sequence set forth in SEQ ID NO: 23; HCDR2 comprises the amino acid sequence set forth in SEQ ID NO: 25; and HCDR3 comprises the amino acid sequence set forth in SEQ ID NO: 57; and wherein the second antigen binding domain comprises a light chain variable domain and a heavy chain variable domain, wherein the light chain variable domain comprises a LCDR1, an LCDR2 and an LCDR3 as shown in any one of SEQ ID NOs: 63-68; and wherein the heavy chain variable domain comprises a HCDR1, an HCDR2 and an HCDR3 as shown in any one of SEQ ID NOs: 69-74.

2. The antibody of claim 1, wherein HCDR3 of the first antigen binding domain comprises an amino acid sequence selected from any of the sequences set forth in SEQ ID NOs: 27, 36, 44 and 49.

3. The antibody of claim 1, wherein:
(a) the first antigen binding domain has a light chain variable domain which comprises a Light Chain Framework Region (LCFR)1 comprising the amino acid sequence as set forth as one of SEQ ID NOs: 15, 29, 50 and 53; an LCFR2 comprising the amino acid sequence as set forth as one of SEQ ID NOs: 17, 30, 38 and 46; an LCFR3 comprising the amino acid sequence as set forth as one of SEQ ID NOs: 19, 31, 39, 47 and 54; and an LCFR4 comprising the amino acid sequence as set forth as one of SEQ ID NOs: 21, 32 and 40, wherein the sequence of each framework region may differ from the given sequence at up to five amino acid positions; or
(b) the first antigen binding domain has a light chain variable domain which comprises an LCFR1 comprising the amino acid sequence as set forth as one of SEQ ID NOs: 29, 50 and 53; an LCFR2 comprising the amino acid sequence as set forth as one of SEQ ID NOs: 30, 38 and 46; an LCFR3 comprising the amino acid sequence as set forth as one of SEQ ID NOs: 31, 39, 47 and 54; and an LCFR4 comprising the amino acid sequence as set forth as one of SEQ ID NOs: 32 and 40, wherein the sequence of each framework region may differ from the given sequence at up to five amino acid positions.

4. The antibody of claim 1, wherein:
(a) the first antigen binding domain has a heavy chain variable domain which comprises a Heavy Chain Framework Region (HCFR)1 comprising the amino acid sequence as set forth as one of SEQ ID NOs: 22, 33, 41 and 55; an HCFR2 comprising the amino acid sequence as set forth as one of SEQ ID NOs: 24, 34, 42 and 51; an HCFR3 comprising the amino acid sequence as set forth as one of SEQ ID NOs: 26, 35, 43, 48, 52 and 56; and an HCFR4 comprising the amino acid sequence as set forth as one of SEQ ID NOs: 28, 37 and 45, wherein the sequence of each framework region may differ from the given sequence at up to five amino acid positions; or
(b) the first antigen binding domain has a heavy chain variable domain which comprises an HCFR1 comprising the amino acid sequence as set forth as one of SEQ ID NOs: 33, 41 and 55; an HCFR2 comprising the amino acid sequence as set forth as one of SEQ ID NOs: 34, 42 and 51; an HCFR3 comprising the amino acid sequence as set forth as one of SEQ ID NOs: 35, 43, 48, 52 and 56; and an HCFR4 comprising the amino acid sequence as set forth as one of SEQ ID NOs: 37 and 45, wherein the sequence of each framework region may differ from the given sequence at up to five amino acid positions.

5. The antibody of claim 1, wherein:
(a) the light chain variable domain of the first antigen binding domain comprises the amino acid sequence as set forth as one of SEQ ID NOs: 3, 4, 5, 6, 7 and 8, or a sequence having at least 90% identity thereto;
(b) the light chain variable domain of the first antigen binding domain comprises the amino acid sequence as set forth as one of SEQ ID NOs: 4, 5, 6, 7 and 8, or a sequence having at least 90% identity thereto;
(c) the heavy chain variable domain of the first antigen binding domain comprises the amino acid sequence as set forth as one of SEQ ID NOs: 9, 10, 11, 12, 13 and 14, or a sequence having at least 90% identity thereto; or
(d) the heavy chain variable domain of the first antigen binding domain comprises the amino acid sequence as set forth as one of SEQ ID NOs: 10, 11, 12, 13 and 14, or a sequence having at least 90% identity thereto.

6. The antibody of claim 1, wherein:
(a) the light chain variable domain of the first antigen binding domain comprises the amino acid sequence as set forth as one of SEQ ID NOs: 4, 5, 6, 7 and 8, or a sequence having at least 90% identity thereto; and
the heavy chain variable domain of the first antigen binding domain comprises the amino acid sequence as set forth as one of SEQ ID NOs: 10, 11, 12, 13 and 14, or a sequence having at least 90% identity thereto; or
(b) the light chain variable domain of the first antigen binding domain comprises the amino acid sequence as set forth as SEQ ID NO: 4 or a sequence having at least 90% identity thereto, and the heavy chain variable domain of the first antigen binding domain comprises the amino acid sequence as set forth as one of SEQ ID NOs: 10, 12 and 13 or a sequence having at least 90% identity thereto; or
(c) for the first antigen binding domain:
(i) the light chain variable domain comprises the amino acid sequence as set forth as SEQ ID NO: 4 and the heavy chain variable domain comprises the amino acid sequence as set forth as SEQ ID NO: 10;
(ii) the light chain variable domain comprises the amino acid sequence as set forth as SEQ ID NO: 5 and the heavy chain variable domain comprises the amino acid sequence as set forth as SEQ ID NO: 11;
(iii) the light chain variable domain comprises the amino acid sequence as set forth as SEQ ID NO: 6 and the heavy chain variable domain comprises the amino acid sequence as set forth as SEQ ID NO: 12;
(iv) the light chain variable domain comprises the amino acid sequence as set forth as SEQ ID NO: 7 and the heavy chain variable domain comprises the amino acid sequence as set forth as SEQ ID NO: 13; or
(v) the light chain variable domain comprises the amino acid sequence as set forth as SEQ ID NO: 8 and the heavy chain variable domain comprises the amino acid sequence as set forth as SEQ ID NO: 14,
wherein each light chain variable domain and heavy chain variable domain above may have at least 90% identity to the amino acid sequence set forth above.

7. A bispecific antibody comprising a first antigen binding domain which selectively binds to Receptor Tyrosine Kinase Like Orphan Receptor 1 (ROR1); and
a second antigen binding domain which selectively binds to the CD3 subunit of the T-Cell Receptor (TCR), wherein for the first antigen binding domain:
(a) the light chain variable domain comprises the amino acid sequence as set forth as SEQ ID NO: 3 and the heavy chain variable domain comprises the amino acid sequence as set forth as SEQ ID NO: 9;
(b) the light chain variable domain comprises the amino acid sequence as set forth as SEQ ID NO: 4 and the heavy chain variable domain comprises the amino acid sequence as set forth as SEQ ID NO: 10;
(c) the light chain variable domain comprises the amino acid sequence as set forth as SEQ ID NO: 5 and the heavy chain variable domain comprises the amino acid sequence as set forth as SEQ ID NO: 11;

(d) the light chain variable domain comprises the amino acid sequence as set forth as SEQ ID NO: 6 and the heavy chain variable domain comprises the amino acid sequence as set forth as SEQ ID NO: 12;

(e) the light chain variable domain comprises the amino acid sequence as set forth as SEQ ID NO: 7 and the heavy chain variable domain comprises the amino acid sequence as set forth as SEQ ID NO: 13; or the light chain variable domain comprises the amino acid sequence as set forth as SEQ ID NO: 8 and the heavy chain variable domain comprises the amino acid sequence as set forth as SEQ ID NO: 14; and, wherein for the second antigen binding domain:

(a) the light chain variable domain comprises the amino acid sequence as set forth as SEQ ID NO: 63 and the heavy chain variable domain comprises the amino acid sequence as set forth as SEQ ID NO: 69;

(b) the light chain variable domain comprises the amino acid sequence as set forth as SEQ ID NO: 64 and the heavy chain variable domain comprises the amino acid sequence as set forth as SEQ ID NO: 70;

(c) the light chain variable domain comprises the amino acid sequence as set forth as SEQ ID NO: 65 and the heavy chain variable domain comprises the amino acid sequence as set forth as SEQ ID NO: 71;

(d) the light chain variable domain comprises the amino acid sequence as set forth as SEQ ID NO: 66 and the heavy chain variable domain comprises the amino acid sequence as set forth as SEQ ID NO: 72;

(e) the light chain variable domain comprises the amino acid sequence as set forth as SEQ ID NO: 67 and the heavy chain variable domain comprises the amino acid sequence as set forth as SEQ ID NO: 73; or (f) the light chain variable domain comprises the amino acid sequence as set forth as SEQ ID NO: 68 and the heavy chain variable domain comprises the amino acid sequence as set forth as SEQ ID NO: 74.

8. The antibody of claim 1, wherein the light chain variable domain of the second antigen binding domain comprises the amino acid sequence as set forth as one of SEQ ID NOs: 63, 64, 65, 66, 67 and 68, or a sequence having at least 90% identity thereto, and wherein the heavy chain variable domain of the second antigen binding domain comprises the amino acid sequence as set forth as one of SEQ ID NOs: 69, 70, 71, 72, 73 and 74, or a sequence having at least 90% identity thereto.

9. The antibody of claim 1 or 7, wherein:
(a) the first antigen binding domain is a scFv antibody;
(b) the second antigen binding domain is a scFv antibody; or
(c) the first and second antigen binding domains are scFv antibodies covalently linked by a peptide linker.

10. The antibody of claim 1 or 7, wherein the antibody comprises the sequence of SEQ ID NO. 75 or 76, or a sequence having at least 90% sequence identity thereto.

11. The antibody of claim 1 or 7, wherein:
(i) the antibody is an IgG or an IgM, and/or
(ii) wherein the antibody is an $IgG_1$ or an $IgG_2$.

12. A pharmaceutical composition comprising the antibody of claim 1 or 7, and a pharmaceutically acceptable carrier.

13. An isolated nucleic acid encoding the antibody of claim 1 or 7.

14. An isolated host cell transformed with a nucleic acid encoding the antibody of claim 1 or 7.

15. A method for treating a ROR1-expressing cancer, the method comprising administering to a subject in need thereof, a therapeutically effective amount of an antibody of claim 1 or 7, and thereby treating the ROR1-expressing cancer.

16. The method of claim 15, wherein the ROR1-expressing cancer is leukaemia, pancreatic cancer, prostate cancer, colon cancer, bladder cancer, ovarian cancer, glioblastoma, testicular cancer, uterine cancer, adrenal cancer, breast cancer, lung cancer, melanoma, neuroblastoma, sarcoma or renal cancer.

* * * * *